(12) United States Patent
Kuroiwa et al.

(10) Patent No.: US 7,402,729 B2
(45) Date of Patent: Jul. 22, 2008

(54) HUMAN ARTIFICIAL CHROMOSOME CONTAINING HUMAN ANTIBODY λ LIGHT CHAIN GENE AND NON-HUMAN ANIMAL CONTAINING THE HUMAN ARTIFICIAL CHROMOSOME CAPABLE OF GENETIC TRANSMISSION

(75) Inventors: Yoshimi Kuroiwa, Sioux Falls, SD (US); Kazuma Tomizuka, Takasaki (JP); Hitoshi Yoshida, San Diego, CA (US); Isao Ishida, Shibuya-ku (JP)

(73) Assignee: Kirin Pharma Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/151,227

(22) Filed: Jun. 14, 2005

(65) Prior Publication Data

US 2006/0015958 A1 Jan. 19, 2006

Related U.S. Application Data

(62) Division of application No. 10/477,471, filed as application No. PCT/JP02/04587 on May 10, 2002.

(30) Foreign Application Priority Data

May 11, 2001 (JP) ............................. 2001-142371

(51) Int. Cl.
*A01K 67/027* (2006.01)
*A01K 67/033* (2006.01)
*C12P 21/00* (2006.01)

(52) U.S. Cl. .............................. 800/18; 800/13; 800/4; 800/6

(58) Field of Classification Search ................... 800/18, 800/13, 4, 6
See application file for complete search history.

(56) References Cited

U.S. PATENT DOCUMENTS

| | | | |
|---|---|---|---|
| 4,959,317 A | 9/1990 | Sauer | |
| 5,270,201 A | 12/1993 | Richards et al. | |
| 5,543,319 A | 8/1996 | Fournier et al. | |
| 5,614,396 A | 3/1997 | Bradley et al. | |
| 6,025,155 A | 2/2000 | Hadlaczky et al. | |
| 6,395,487 B1 | 5/2002 | Bradley et al. | |
| 6,461,818 B1 | 10/2002 | Bradley et al. | |
| 6,632,976 B1 | 10/2003 | Tomizuka et al. | |
| 7,041,870 B2 * | 5/2006 | Tomizuka et al. | ............. 800/13 |

FOREIGN PATENT DOCUMENTS

| | | |
|---|---|---|
| EP | 0 773 288 A2 | 5/1997 |
| EP | 0 843 961 A1 | 5/1998 |
| EP | 0 972 445 A1 | 1/2000 |
| EP | 1 106 061 A1 | 6/2001 |
| JP | 2001-231403 | 8/2001 |
| JP | 2001-231403 A | 8/2001 |
| WO | WO 89/09219 A1 | 10/1989 |
| WO | WO 91/19796 | 12/1991 |
| WO | WO 95/32297 | 11/1995 |
| WO | WO 97/49804 | 12/1997 |
| WO | WO 98/46733 | 12/1998 |
| WO | WO 98/54348 | 12/1998 |
| WO | WO 00/10383 | 3/2000 |

OTHER PUBLICATIONS

Nicholson et al, Journal of Immunology 163:6898-6906, 1999.*
Kazuma Tomizuka et al., "Functional expression and germline transmission of a human chromosome fragment in chimaeric mice", Nature Genetics, vol. 16, p. 133-143 (1997).
E.S. Dieken et al., "Efficient modification of human chromosomal alleles using recombination-proficient chicken/human microcell hybrids", Nature Genetics, vol. 12, p. 174-182 (1996).
A.J.H. Smith et al., "A site-directed chromosomal translocatin induced in embryonic stem cells by Cre-IoxP recombination" Nature Genetics, vol. 9, pp. 376-385 (1995).
I. Wilmut et al., "Viable offspring derived from fetal and adult mammalian cells", Nature, vol. 385, p. 810 (1997).
R. Ramiriz-Solis et al., "Chromosome engineering in mice", Nature, vol. 378, pp. 720-724 (1995).
W. Mills et al, "Generation of an ~2.4 Mb human X centromere-based minichromosome by targeted telomere-associated chromosome fragmentation in DT40", Human Molecular Genetics, vol. 8, No. 5, p. 751-761 (1999).
C.J. Farr et al., "Generation of a human X-derived minichromosome using telomere-associated chromosome fragmentation", The EMBO Journal, vol. 14, No. 21, pp. 5444-5454 (1995).
M. H. Shen et al., "Human mini-chromosomes in mouse embryonal stem cells", Human Molecular Genetics, vol. 6, No. 8, pp. 1375-1382, (1997).

(Continued)

*Primary Examiner*—Anne Marie Wehbé
(74) *Attorney, Agent, or Firm*—Baker Botts LLP

(57) ABSTRACT

The present invention relates to a human artificial chromosome which is genetically transmissible to the next generation with high efficiency and the method for using the same. More specifically, the present invention relates to: a human artificial chromosome in which an about 3.5 Mb to about 1 Mb region containing an antibody λ light chain gene derived from human chromosome 22 is bound to a chromosome fragment which is transmissible to a progeny through a germ line of a non-human animal, said chromosome fragment is derived from another human chromosome; a non-human animal carrying the human artificial chromosome and an offspring thereof; a method for producing the non-human animal; a method for producing a human antibody using the nonhuman animal or an offspring thereof; and a human antibody-producing mouse carrying the human artificial chromosome.

10 Claims, 4 Drawing Sheets

OTHER PUBLICATIONS

W. Brown et al., "Mammalian artificial chromosomes", Genetics of disease, pp. 281-288.

M. Qin et al., "Cre recombinase-mediated site-specific recombination between plant chromosomes", Proc. Natl. Acad. Sci. USA, vol. 91, p. 1706-1710 (1994).

M. Koi et al., "Tumor Cell Growth Arrest Caused by Subchromosomal Transferable DNA Fragments fom Chromosome 11", Science, vol. 260 (1993).

A.E. Schnieke et al., Human Factor IX Transgenic Sheep Produced by Transfer of Nuclei from Transfected Fetal Fibroblasts, Science, vol. 278 (1997).

J.B. Cibelli et al., "Cloned Transgenic Calves Produced from Nonquiescent Fetal Fibroblasts", Science, vol. 280 (1998).

Y. Kuroiwa et al., "Efficient modification of a human chromosome by telomere-directed truncation in high homologous recombinant-proficieint chicken DT40 cells", Nucleic Acids Research, vol. 26, No. 14, pp. 3447-3448 (1998).

B. Grimes et al., "Engineering mammalian chromosomes", Human Molecular Genetics, vol. 7, No. 10, Review, p. 1635-1640 (1998).

M. Brüggemann et al., "Production of human antibody repertoires in transgenic mice", Current Opinion in Biotechnology, 8 pp. 455-458 (1997).

M. Taniguchi et al., "Efficient production of Cre-mediated site-directed recombinants through the utilization of the puromycin resistance gene, pac: a transient gene-integration marker for ES cells", Nucleic Acids Research, vol. 26, No. 2, pp. 679-680 (1998).

J.C. Vasquez et al., "Factors for affecting the efficiency of introducing precise genetic changes in ES cells by homologous recombination: tag-and-exchange versus the Cre-loxp system", Transgenic Research, vol. 7, pp. 181-193 (1998).

S. Gagneten et al., "Brief expression of a GFP cre fusion gene in embryonic stem cells allows rapid retrieval of site-specific genomic deletions", Nucleic Acids Research, vol. 25, No. 16, pp. 3326-3331 (1997).

N.P. Davies et al., "Creation of Mice Expressing Human Antibody Light Chains by Introduction of a Yeast Artificial Chromosome Containing the Core Region of the Human Immunoglobulin κ Locus", Bio/Technolgoy, vol. 11, pp. 911-914 (1993).

M.J. Mendez et al., "Analysis of the Structural Integrity of YACs Comprising Human Immunoglobulin Genes in Yeast and in Embryonic Stem Cells", Genomics, vol. 26, pp. 294-307 (1995).

H. Cooke, "Non-programmed and Engineered Chromosome Breakage", Cold Spring Harbor Monograph Sereis; Telomeres, pp. 219-245 (1995).

R. Heller et al., "Mini-chromosomes derived from the human Y chromosome by telomere directed chromosome breakage", Proc. Natl. Acad. Sci. USA, vol. 93, pp. 7125-7130 (1996).

K.A. Henning et al., "[7] Techniques and Applications of Microcell-Mediated Chromosome Transfer to Mammalian Cells", Methods in Molecular Genetics, vol. 1, Gene and Chromosome Analysis, Part A, pp. 134-150 (1993).

W.M. Moreadith et al., "Gene targeting in embryonic stem cells: the new physiology and metabolism", J. Mol. Med. , 75, pp. 208-216 (1997).

M.F. Pera et al., "Human embryonic stem cells", Journal of Cell Science, 113, pp. 5-10 (2000).

K. Tomizuka et al., "Functional expression and germline transmission of a human chromosome fragment in chimaeric mice", Nature Genetics, vol. 16, pp. 133-143, (1997).

H-H. Gerdes et al., "Green fluorescent protein: applications in cell biology", FEBS Letters, 389, pp. 44-47 (1996).

International Search Report.

Supplementary Partial European Search Report of EP 02 76 9569.

Shinohara Tokuyuki et al., "Stability of Transferred Human Chromosome Fragments in Cultured Cells and in Mice", Chromosome Research, vol. 8, No. 8, 2000, pp. 713-725.

K. Tomizuka et al., "Double trans-chromosomic mice: maintenance of two individual human chromosome fragments containing Ig heavy and k loci and expression of fully human antibodies", Proceedings of the National Academy of Sciences of USA, National Academy of Science, Washington, US, vol. 97, No. 2, Jan. 18, 2000, pp. 722-727.

Shigeru Araga et al., "Production of monoclonal antibodies (mAb) against human alpha-acetylcholine receptor using KM mice(reg)", FASEB Journal, vol. 16, No. 5, Mar. 22, 2002, p. A1218.

K. Tomizuka et al., "Creation of Mice Producing Human Antibodies by Using Chromosome Vectors", Gekkan Soshiki Baiyo Kogaku—Tissue Culture Engineering, NYU Saiensusha, Tokyo, Japan, vol. 24, No. 14, 1998, p. 1.

Y. Kuroiwa et al., "Manipulation of Human Minichromosomes to Carry Greater than Megabase Sized Chromosome Inserts", Nature Biotechnology, Nature Publishing US, vol. 18, Oct. 2000, pp. 1086-1090.

Supplementary European Search Report of EP 02 76 9569.

Isao Ishida et al., "Production of a Diverse Repertoire of Human Antibodies in Genetically Engineered Mice", Microbial. Immunol. 42(3), 143-150, 1998.

Y. Kuroiwa et al., "The use of chromosome-based vectors for animal transgenesis", Gene Therapy (2002) 9, 708-712.

Jean-Michel H. Vos, "Mammalian artifical chromosomes as tools for gene therapy", Current Opinion in Genetics & Development, Current Biology Ltd., XX, vol. 8, No. 3, 1998, pp. 351-359.

Dionne M. Fishwild et al., "High-avidity human IgGκ monoclonal antibodies from a novel strain of minilocus transgenic mice", Nature Biotechnology, vol. 14, Jul. 1996, pp. 845-851.

Michael J. Mendez et al., "Functional transplant of megabase human immunoglobulin loci recapitulates human antibody response in mice", Nature Genetics, vol. 15, Feb. 1997, pp. 146-156.

* cited by examiner

```
                           SEQUENCE LISTING

<160> NUMBER OF SEQ ID NOS: 16

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 1
tcgaggatcc gacaagttct cttctctttt ccttctgccc                40

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 2
tcgaggatcc gctgctaagc tactgttctc tttttccce                40

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 3
tcgagtcgac tgtagctgac tttagccacc cacaagtac                 39
```

```
<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 4
tcgagtcgac cttgctgatt atacctcatc tccttccctc                              40

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 5
gctaaggcac ttcggttctc tttgtgttc                                          29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 6
ggttgtcttt aaaagcaggg ataaggatg                                          29

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 7
agaagaaagg agtgggtgct aaacattcag                                         30

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 8
ggttagatgg caccaaatga aaggagaag                                          29

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 9
agtgagataa gcagtggatg                                                    20

<210> SEQ ID NO 10
<211> LENGTH: 20
<212> TYPE: DNA
<213> ORGANISM: Artificial Sequence
<220> FEATURE:
```

```
<223> OTHER INFORMATION: Description of Artificial Sequence:primer

<400> SEQUENCE: 10
gttgtgctac tcccatcact                                                   20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 11
gagagttgca gaaggggtga ct                                                22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 12
ggagaccacc aaaccctcca aa                                                22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 13
atagcagctt tgctccttcg                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 14
ttctctcctg cacatagccc                                                   20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 15
tgttctcctc ttcctactct cc                                                22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 16
tgaaggtagt gaccagtgtt gg                                                22
```

HUMAN ARTIFICIAL CHROMOSOME CONTAINING HUMAN ANTIBODY λ LIGHT CHAIN GENE AND NON-HUMAN ANIMAL CONTAINING THE HUMAN ARTIFICIAL CHROMOSOME CAPABLE OF GENETIC TRANSMISSION

TECHNICAL FIELD

The present invention relates to a human artificial chromosome which can be genetically transmitted to the next generation with high efficiency through modification of a chromosome or a fragment thereof, a non-human animal which genetically transmits the human artificial chromosome to the next generation with high efficiency and an offspring thereof, a method for producing an antibody from the non-human animal or an offspring thereof, and a human antibody-producing mouse.

BACKGROUND ART

A technique has been developed in which a chimeric animal is produced from a hybrid cell obtained by fusion between a microcell containing a chromosome fragment and a pluripotent cell (WO 97/07671). This enabled the production of a non-human animal carrying a very long foreign gene, which was heretofore impossible.

Modification of a chromosome fragment to be introduced into a non-human animal is useful because it realizes (1) removal of unnecessary genes, (2) addition of desired genes, (3) stabilization of a chromosome fragment and the like. WO 98/37757 describes a summary of a method for modifying a chromosome fragment to be introduced into a non-human animal and that a deletion chromosome of interest was obtained with high efficiency by targeting a telomeric sequence to a human chromosome retained in the DT-40 cell derived from a chicken. This publication also describes a fragment of a human chromosome which is stably retained in a mouse ES cell and an individual mouse, and has high genetic transmission efficiency. WO 00/10383 describes a method for producing a more stable human artificial chromosome (hereinafter this may be abbreviated to "HAC") in which a desired region on the human chromosome is translocated to a stable chromosome fragment (chromosome vector).

Recently, Kuroiwa et al. (Nature Biotech. 18: 1086, 2000) succeeded, for the first time in the world, in producing a human artificial chromosome (HAC) retaining a specific human chromosome region of mega base (Mb) size as an insert. This HAC (λHAC) is an artificial chromosome that was obtained by using a SC20 fragment derived from human chromosome 14, which was stable and genetically transmissible, as a chromosome vector, and by translocating and cloning a 10 Mb chromosome region containing a human antibody λ light chain gene on human chromosome 22 to the vector as an insert. They demonstrated that this λHAC had a stability substantially equivalent to that of the SC20 fragment used as a vector and regions derived from various unstable chromosomes could be stabilized by being translocated and cloned to SC20 as well. Further, they introduced this λHAC to a mouse, thereby succeeding in producing a chimeric mouse which stably carried λHAC.

In a non-human animal, genetic transmission of an introduced human chromosome to the next generation is important not only with regard to mass-production of transchromosomic animals by crossing (i.e., a non-human animal in which heterogenic chromosome fragments have been genetically transmitted through a germ line) having homogeneity, but also with regard to analysis of structures and functions through a germ line of the introduced human chromosome. Several types of human chromosomes have been heretofore introduced into mice and the genetic transmission capacity thereof is considered to depend on the structure of the introduced human chromosome. For the purpose of genetic transmission, at the outset it is essential to obtain a chimeric mouse in which the ES cell contributes with high efficiency to a germ cell and the chimerism is high. This chimerism is considered to be associated with a structure of the introduced human chromosome, that is, which type of human gene is present on the introduced chromosome. For example, when a fragment of human chromosome 2 or 14 is introduced, a chimeric mouse whose chimerism is close to 100% is obtained and its genetic transmission efficiency is high (Tomizuka et al., Proc. Natl. Acad. Sci. USA, 97: 722-727, 2000). In contrast, when a fragment of human chromosome 22 is introduced, a chimeric mouse whose chimerism is low, i.e., 50% or below, is obtained in most cases. This may be because a harmful human gene that adversely affects the development of a mouse is present on human chromosome 22. In fact, it is reported that gene expression-level-dependent hereditary disease-causing regions such as cat's eye syndrome, DiGeorge syndrome, and der22 syndrome exist in the 22q11 region on human chromosome 22 where the human antibody Ig λ gene is present (for example, A. Puech et al., PNAS 97: 10090, 2000). As described above, these hereditary disease-causing regions are removed, and only 10 Mb from the HCF2 locus to the LIF locus on human chromosome 22 is translocated and cloned to the SC20 chromosome vector to construct λHAC, followed by introduction into a mouse. As a result, the chimerism of the chimeric mouse generated from the ES cell retaining λHAC is reported to be enhanced compared to the case where the full length of human chromosome 22 was introduced.

Under the above circumstances, the present inventors have attempted to further improve the human artificial chromosome in order to achieve more efficient genetic transmission than the conventional λHAC, and have studied the genetic transmission efficiency.

More specifically, an object of the present invention is to provide a human artificial chromosome which is genetically transmissible to the next generation with high efficiency by modification of human chromosome 22 or a fragment thereof, and a non-human animal carrying the human artificial chromosome and an offspring thereof.

Another object of the present invention is to provide a method for producing a human antibody using the non-human animal or an offspring thereof.

The present inventors have conducted concentrated studies in order to attain the above objects. As a result, they have modified human chromosome 22, selected two types of regions with a clear construction containing an antibody λ light chain gene (Ig λ) region, and constructed a human artificial chromosome in which each of the selected regions was translocated to a fragment of human chromosome 14, thereby producing a mouse with a high chimerism carrying the same. As a result, the present inventors observed that the human artificial chromosome was genetically transmitted to the offspring at the next generation with high efficiency through meiosis in the chimeric mouse, thereby completing the present invention.

DISCLOSURE OF THE INVENTION

The subject matters of the present invention are as follows.

One aspect of the present invention provides a human artificial chromosome, wherein an about 3.5 Mb to about 1 Mb region containing an antibody λ light chain gene derived from human chromosome 22 is bound to a chromosome fragment which is transmissible to a progeny through a germ line of a non-human animal, said chromosome fragment is derived from another human chromosome.

According to one embodiment, the chromosome fragment derived from another human chromosome may be any fragment of a human chromosome as long as it is stable and genetically transmissible. For example, a chromosome fragment may be a fragment of human chromosome 14, human chromosome 21 or a fragment thereof, or a small accessory chromosome (SAC) containing the lp22 region of human chromosome 1 (Genome Res., 11: 124-136, 2001), and it may be preferably a fragment of human chromosome 14, for example, SC20 chromosome vector derived from human chromosome 14 (Kuroiwa et al., described above). The SC20 chromosome vector can be used for cloning a chromosome fragment of interest by, for example, inserting a loxP sequence by homologous recombination into the RNR2 locus located at the 14p12 site (Kuroiwa et al., described above). A chicken DT-40 cell (SC20) retaining the SC20 chromosome vector was deposited internationally at the International Patent Organism Depositary of the National Institute of Advanced Industrial Science and Technology (Tsukuba Central 6, 1-1-1 Higashi, Tsukuba, Ibaraki, Japan) as of May 9, 2001 under the accession number of FERM BP-7583. The chromosome fragment derived from another human chromosome can be also obtained in accordance with a method disclosed in WO 97/07671, preferably by producing a chimeric non-human animal carrying various human chromosome fragments having a size of about 20 Mb or smaller and selecting a fragment that is stably carried by the offspring of the chimeric non-human animal. A region containing the antibody λ light chain gene derived from human chromosome 22 is bound to a genetically transmissible human chromosome fragment by translocation or insertion mediated by a site-specific recombinant sequence such as loxP sequence. When the region containing the antibody λ light chain gene is cleaved out with the telomeric sequence and the loxP sequence as the two ends, as described in the examples below, binding by translocation occurs. In contrast, when the region containing the antibody λ light chain gene is cleaved out by inserting the loxP sequences at the two ends, insertion into the loxP sequence site on the genetically transmissible human chromosome fragment occurs.

According to another embodiment, the size of the region containing the antibody λ light chain gene derived from human chromosome 22 is about 2.5 Mb to about 1.5 Mb.

According to a further embodiment, the size of the region containing the antibody λ light chain gene derived from human chromosome 22 is about 2.5 Mb or about 1.5 Mb. Specific examples of regions having such sizes are human artificial chromosomes respectively comprising ΔHAC retained in a chicken DT-40 cell (ΔHAC) under the accession number of FERM-BP-7582 and ΔΔHAC retained in a chicken DT-40 cell (ΔΔHAC) under the accession number of FERM-BP-7581 (see the examples below).

Another aspect of the present invention provides a non-human animal carrying the human artificial chromosome of the present invention. In the present specification, the term "non-human animal" refers to a vertebrate other than a human and preferably refers to a mammal.

According to one embodiment, the non-human animal carries either ΔHAC or ΔΔHAC human artificial chromosome.

According to another embodiment, the non-human animal is a mammal. Preferably, a mammal is a mouse.

A further aspect of the present invention provides a method for producing a non-human animal, which comprises: introducing the human artificial chromosome of the present invention into an embryonic stem cell (ES cell) of a non-human animal by a microcell method; injecting the obtained ES cell into an embryo of the non-human animal; transplanting the resulting injected embryo to a foster parent; obtaining a chimeric non-human animal from the foster parent by parturition; and screening the chimeric non-human animal for the human artificial chromosome.

In introduction into the ES cell, a Chinese hamster ovarian (CHO) cell retaining a human artificial chromosome may be produced to introduce the human artificial chromosome into the ES cell through the CHO cell.

According to one embodiment, the above-described method further comprises producing an offspring of the screened chimeric non-human animal and screening the offspring for the human chromosome.

According to another embodiment, the non-human animal obtained by the above method is capable of expressing human antibody immunoglobulin heavy chain and λ chain proteins.

According to a further embodiment, the non-human animal is a mammal, and is preferably a mouse.

A further aspect of the present invention provides a non-human animal carrying the human artificial chromosome of the present invention, which can be obtained by the method of the present invention.

A further aspect of the present invention provides an offspring animal of the non-human animal of the present invention. The offspring animal carries the human artificial chromosome of the present invention.

According to one embodiment, the offspring animal is capable of expressing human antibody immunoglobulin heavy chain and λ light chain proteins.

According to another embodiment, the offspring animal is capable of expressing human antibody immunoglobulin heavy chain, κ light chain, and λ light chain proteins.

According to a further embodiment, the offspring animal is a mouse.

A further aspect of the present invention provides a method for producing an antibody, which comprises: immunizing the non-human animal of the present invention or the offspring animal of the present invention with a desired antigen; and obtaining a human polyclonal antibody against the antigen from the animal.

According to one embodiment, the human polyclonal antibody is obtained from blood of the animal.

A further aspect of the present invention provides a method for producing an antibody, which comprises: immunizing the mouse of the present invention or the offspring mouse of the present invention with a desired antigen; producing a hybridoma by fusing a spleen cell of the mouse with a mouse myeloma cell; and producing a human monoclonal antibody consisting of human immunoglobulin heavy chain and light chain against the antigen.

A further aspect of the present invention provides a method for producing an antibody, which comprises: immunizing the mouse of the present invention or the offspring mouse of the present invention with a desired antigen; producing a hybridoma by fusing a spleen cell of the mouse with a mouse myeloma cell; isolating a human antibody gene from the hybridoma; introducing the human antibody gene into an animal cell, a yeast cell, or an insect cell; culturing the cell under conditions capable of expressing a human antibody gene; and producing a human monoclonal antibody consisting of human immunoglobulin heavy chain and light chain against the antigen.

A further aspect of the present invention provides a method for producing an antibody, which comprises: immunizing the mouse of the present invention or the offspring mouse of the present invention with a desired antigen; selecting an antibody gene derived from a B-cell of the mouse by a phage display method; introducing the selected human antibody gene into an animal cell, a yeast cell, or an insect cell; culturing the cell under conditions capable of expressing a human antibody gene; and producing a human monoclonal antibody consisting of human immunoglobulin heavy chain and light chain against the antigen.

The method for expressing can be carried out in accordance with a conventional method (for example, a method described in Sambrook et al., Molecular Cloning, A Laboratory Manual, Second Edition, (1989) Cold Spring Harbor Laboratory Press). An animal cell, a yeast cell, or an insect cell as a host includes, for example, a CHO cell, a BHK cell, a liver carcinoma cell, a myeloma cell, a baker's yeast cell, and an SF9 cell.

A further aspect of the present invention provides a human antibody-producing mouse which expresses a human antibody heavy chain comprising a human antibody Ig γ isotype, a human antibody κ light chain, and a human antibody λ light chain in serum. The human antibody-producing mouse carries a unrearranged human antibody heavy chain locus, a human antibody κ light chain locus, and a human antibody λ light chain locus, and at least both alleles of endogenous antibody heavy chain and κ light chain are disrupted or inactivated.

In the above human antibody-producing mouse, linkage of segments of specific variable regions occurs by the rearrangement of human antibody genes upon B cell differentiation (V-D-J in the heavy chain, V-J in the light chain). Preferably, after somatic mutagenesis in the variable region of antibody genes upon B cell maturation, a human antibody as the gene product is produced in serum.

Specifically, the term "unrearranged" refers to a state in which an antibody locus is capable of V-D-J recombination in a heavy chain and V-J recombination in a light chain upon B cell differentiation whereas either V-D-J recombination in the heavy chain or V-J recombination in the light chain have not been occurred, and the antibody locus is retained in an undifferentiated B cell of a mouse.

In one embodiment, the human antibody-producing mouse carries at least 40% of the variable region of the human antibody κ light chain.

In another embodiment, the human antibody-producing mouse carries all the variable regions of the human antibody heavy chain, the human antibody κ light chain, and the human antibody λ light chain.

In a further embodiment, the human antibody heavy chain locus, the human antibody κ light chain locus, and the human antibody λ light chain locus are retained on a chromosome fragment derived from a human.

In a further embodiment, a human antibody heavy chain locus and a human antibody λ light chain locus are retained on either ΔHAC or ΔΔHAC human artificial chromosome.

In a further embodiment, the human antibody κ light chain locus is retained on a chromosome fragment derived from a human.

In a further embodiment, the human antibody κ light chain locus is inserted into a mouse chromosome.

In a further embodiment, the human antibody-producing mouse is not a chimeric mouse. Preferably, the human antibody-producing mouse is capable of genetic transmission of the human antibody heavy chain locus, the human antibody κ light chain locus, and the human antibody λ light chain locus.

1. Production and Use of Human Artificial Chromosome (HAC) and Transchromosomic Non-Human Animal The present invention relates to: construction of a novel human artificial chromosome that is prepared by translocating and cloning a fragment containing the Ig λ gene on human chromosome 22 to a chromosome fragment derived from human chromosome 14; genetic transmission of the human artificial chromosome in a mouse; and production of a transchromosomic non-human animal carrying the human artificial chromosome (for example, a mammal such as a mouse).

In the present specification, the human artificial chromosome. (HAC) refers to an artificial chromosome produced by translocating a desired region on the human chromosome to a stable chromosome fragment (chromosome vector). The term "transchromosomic non-human animal" refers to an animal other than a human in which the chromosome fragment from different species has been genetically transmitted through a germ line.

The human artificial chromosome is produced as a human artificial chromosome retaining only the periphery of the gene region of interest as an insert (chromosome insert) by, for example, inserting a loxP sequence and a human telomeric sequence into the vicinity of the gene region of interest on the human chromosome through homologous recombination, and specifically translocating only the periphery of the gene region of interest sandwiched between the two sequences into the corresponding loxP sequence-inserted site on the other chromosome fragment (a chromosome fragment is preferably stable and genetically transmissible; for example, SC20 chromosome vector derived from human chromosome 14) (Kuroiwa et al., Nature Biotech., 18: 1086, 2000).

In the production of a human artificial chromosome, the present inventors considered that a chromosome region which is presumed to adversely affect development of a chromosome-introduced animal is preferably removed from the chromosome insert as much as possible so as not to adversely affect the development of a chromosome-introduced animal such as a mouse. However, since there has been heretofore little or no information on the structure of a human chromosome such as detailed sequences, it was sometimes difficult to insert, for example, a loxP sequence and a human telomeric sequence in the vicinity of the gene of interest. In this case, since many genes other than the gene of interest are contained in the region sandwiched between both sequences, there was a fear that when these extra genes were introduced into a mouse and the like, they might adversely affect the development. Further, a correlation between the size of a chromosome insert containing a gene of interest and the chimerism and genetic transmission efficiency of the chromosome-introduced animal was not clear.

The present inventors have now found that the chimerism and the genetic transmission efficiency of the chromosome-introduced animal significantly increase for the Ig λ gene-containing chromosome insert in a given size range based on information on the structure of human chromosome 22 in which the Ig λ gene is present (for example, I. Dunham et al., Nature 402: 489, 1999). Thus, removal of extra genes from the human artificial chromosome enabled the production of a novel human artificial chromosome retaining a specified periphery of the Ig λ gene region as an insert. In the present specification, the term "extra genes" refers to harmful genes which adversely affect the development of chromosome-introduced animals, and examples thereof include gene expression-level-dependent hereditary disease-causing regions. The human artificial chromosome of the present invention has a reduced size as a whole and higher genetic transmission efficiency compared to the conventional λHAC retaining a periphery of the Ig λ gene region (10 Mb) as an insert.

Thus, modification of human chromosome 22 enables the production of a human artificial chromosome retaining only a specific Ig λ gene region of interest as an insert from which harmful genes capable of adversely affecting the development of a mouse and the like are removed. As a result of the modification, the introduced human artificial chromosome has a reduced size as a whole, and an elimination mechanism (for example, P. Hunt et al., Hum. Mol. Genet., 4: 2007, 1995) of abnormal chromosomes (in this case, introduced human artificial chromosome) at the time of meiosis can be also avoided. Further, transmission of the introduced human artificial chromosome to an offspring of the human artificial chromosome-introduced animal (for example, a mouse) is facilitated compared to the conventional λHAC (Kuroiwa et al., above-mentioned), and a transchromosomic non-human animal carrying a entire region of human antibody heavy chain and λ light chain can be more efficiently produced.

The transchromosomic non-human animal thus obtained can be used to express a gene on the foreign chromosome or a fragment thereof, and the product thereof is collected, thereby producing a biologically active substance. More specifically, the individual transchromosomic non-human animal is bred under conditions in which a gene on the foreign chromosome or a fragment thereof can be expressed, and the expressed product can be then collected from blood, ascites or the like of the animal.

Tissues, cells, or immortalized cells (for example, a hybridoma immortalized by fusion with a myeloma cell) of the transchromosomic non-human animal, or the like are cultured under conditions in which a gene on the foreign chromosome or a fragment thereof can be expressed, and the expression product can be then collected from the culture product.

Alternatively, the foreign chromosome or a fragment thereof extracted from tissues, cells, or immortalized cells of these transchromosomic non-human animals, DNA constructing the foreign chromosome or a fragment thereof, or cDNA derived from the foreign chromosome or a fragment thereof retained on tissues, cells, or immortalized cells of the transchromosomic non-human animal is introduced into an animal cell, a yeast cell, or an insect cell (for example a CHO cell, a BHK cell, a liver carcinoma cell, a myeloma cell, a baker's yeast cell, or an SF9 cell), the cell is cultured under conditions in which the gene on the foreign chromosome or a fragment thereof can be expressed, and the expressed product (for example, an antibody protein specific to a specified antigen) can be then collected from the culture product. The expressed product can be collected in accordance with a conventional method such as centrifugation. Further, it can be purified in accordance with a conventional method such as ammonium sulfate fractionation, partition chromatography, gel filtration chromatography, adsorption chromatography, or preparative thin layer chromatography. Biologically active substances include all substances coded on the foreign chromosome, and examples thereof include an antibody and, in particular, a human antibody. For example, a human antibody gene on the chromosome can be cloned from a spleen cell obtained transchromosomic non-human animal or an immortalized cell thereof such as a hybridoma, and introduced into a Chinese hamster ovarian cell (CHO) or a myeloma cell, thereby producing a human antibody (Lynette et al., Biotechnology, 10: 1121, 1992; Bebbington et al., Biotechnology, 10: 169, 1992; Babcook et al., PNAS, 93: 7843, 1996).

In addition to the conventional method for selecting a desired antibody-producing cell by selecting a hybridoma, a desired antibody can be selected by the phage display method that was recently developed (Winter et al., Annu. Rev. Immunol., 12: 433, 1994). In order to obtain a phage library which expresses on its surface human antibodies with various specificities, cDNA of variable region in human immunoglobulin heavy chain and light chain derived from a spleen or lymphatic tissue of the transchromosomic non-human animal of the present invention which has not been sensitized to any antigen or has been sensitized to a specific antigen, can be used.

A method for producing a human artificial chromosome having high genetic transmission efficiency is described below in more detail.

In order to produce a non-human animal that comprises a human chromosome region of interest, stably carries it, and genetically transmits it, a technique for processing a chromosome at will is required instead of using an incidentally-generated chromosome fragment. For example, a human chromosome is cleaved at a desired site to remove a harmful gene, or only a desired chromosome fragment is linked to another chromosome that is stable and genetically transmissible. Such a technique is referred to as "chromosome engineering." Up to now, mainly in this technique an endogenous mouse chromosome was cleaved in a site-specific manner in a mouse ES cell (WO 98/54348) or recombination (translocation) between homologous chromosomes was caused to delete, invert, or multiply a specific gene region. Thus, a variant mouse having such a modified chromosome has been produced (R. Ramirez-Solis et al., Nature 378: 720, 1995). This technique can be also applied to the present invention.

When a non-human animal with a high chimerism (for example, a mammal such as a mouse) in which the ES cell retaining a human chromosome or a fragment thereof contributes to a germ cell is obtained, whether or not sperm or egg retaining the introduced human chromosome is formed without the introduced human chromosome being removed at the time of meiosis is the next issue of concern. As described above, it is generally considered that an abnormal chromosome is removed at the time of meiosis. Thus, it is possible that cells retaining the introduced human chromosome are removed at the time of meiosis and as a result those cells may not be differentiated into sperm or egg. This is because although pairing between homologous chromosomes is required at the time of meiosis, there is only one introduced human chromosome. Thus, paring is basically impossible. Accordingly, the introduced human chromosome may be excluded from meiosis. In fact, Tomizuka et al. (Nature Genet., 16: 133, 1997) reported that introduction of approximately 50 Mb or more fragments of human chromosome 14 resulted in sterility in a chimeric male mouse. In contrast, in genetic transmission of a fragment of human chromosome 2 or 14 (SC20), the size of which is presumed to be about 10 to 20 Mb, the size of the introduced chromosome was suggested to be an important factor for passing meiosis (Tomizuka et al., Nature Genet., 16: 133, 1997, Proc. Natl. Acad. Sci. USA., vol. 97, 722-727, 2000). The SC20 chromosome vector (10 to 20 Mb) is genetically transmissible and is also highly stable in the mouse ES cell and an individual mouse (Shinohara et al., Chromosome Res., 8: 713-725, 2000). The naturally occurring chromosome fragment which is genetically transmissible and is stable in an individual mouse can be obtained and selected by methods described in WO 97/07671 and WO 98/37757. A naturally occurring fragment of a human chromosome which is genetically transmissible and is stable in an individual mouse is also described in the report by Voet et al. (Genome Res., 11: 124-136, 2001). Further, human chromosome 14 (about 100 Mb, Tomizuka et al., Nature Genet., 16: 133, 1997) or chromosome 21 (about 50 Mb, Shinohara et al., the 45th Annual Meeting of the Japan Society of Human Genetics, October 2000) stably carried in a chimeric mouse is used as a starting material, and this can be reduced to 10 to 20 Mb or smaller by a chromosome engineering technique (Kuroiwa et al., Nature Biotech. 18: 1086, 2000). According to the present invention, an artificial chromosome can be obtained which is stable in an individual mouse and has high genetic transmission efficiency by reducing the size of the introduced chromosome to a specific size range using the above technique.

For example, HAC which is constructed by translocating and cloning only a gene region of interest in the specific size range to the genetically transmissible SC20 vector becomes genetically transmissible by the effect as a vector of the SC20 fragment. In this case, a stable structure of SC20 may be changed by translocation or the size of HAC as a whole may become larger than the original SC20 vector. Therefore, the size of the chromosome insert to be translocated (containing the immunoglobulin λ gene on human chromosome 22) can be smaller than λHAC (10 Mb), i.e., generally about 3.5 Mb to about 1 Mb, preferably about 3 Mb to about 1.2 Mb, and more preferably about 2.5 Mb to about 1.5 Mb. The end on the centromeric side of the chromosome insert to be translocated is preferably the HCF2 locus, and more preferably an AP000553 region (I. Dunham et al., Nature 402: 489, 1999). Elucidation of the total sequences of the chromosome to be modified such as human chromosome 22 significantly contributes to strict modification of a chromosome as described above. Accordingly, if the sequence of the entire human chromosome is elucidated, genetic transmission can be efficiently carried out by strictly translocating and cloning only the peripheral region containing the gene of interest on human chromosome 22 as well as on various human chromosomes to the SC20 chromosome vector.

As described above, there are several obstacles to achieving genetic transmission of the introduced human chromosome in a non-human animal such as a mouse, and in particular, efficient genetic transmission of the Ig λ gene region on human chromosome 22 has been considered difficult. This problem, however, can be eliminated by the present invention.

Specifically, in the present invention, 2.5 Mb and 1.5 Mb regions containing the antibody λ light chain gene on human chromosome 22 are translocated and cloned to the SC20 chromosome vector to produce a human artificial chromosome (ΔHAC and ΔΔHAC), subsequently, each of ΔHAC and ΔΔHAC is introduced into an individual mouse, and a chimerism in a chimeric mouse is compared to λHAC (Kuroiwa et al., described above), thereby confirming an improvement in the chimerism and achievement of efficient genetic transmission of the human artificial chromosome. The chimerism indicates a contribution ratio of the ES cell in the chimeric animal, and can be generally determined by visually evaluating the ratio of the coat color derived from the ES cell on the surface of the body of the chimeric animal. This specific example is described in more detail.

2. Production and Use of ΔHAC, ΔΔHAC, and Transchromosomic Mouse

Human chromosome 22 containing a human antibody λ light chain gene or a fragment thereof can be obtained by a well-known method. More specifically, a human chromosome or a fragment thereof can be constructed into a library in a mouse A9 cell by a microcell method (Koi et al., Jpn. J. Cancer Res. 80: 413418, 1989). From the resulting library, a sequence specific to a human antibody λ light chain gene can be detected by PCR and the like to select a clone retaining human chromosome 22 or a fragment thereof. For the convenience of later modification, human chromosome 22 or a fragment thereof can be more preferably transferred into the chicken DT-40 cell (RIKEN Cell Bank: RCB 1464, ATCC: CRL-2111) by a microcell method.

A human antibody λ light chain gene cluster exists at 22q 11.2 on chromosome 22 (for example, J. E. Collins et al., Nature 377: 367, 1995). In the above λHAC, a 10 Mb region from the HCF2 locus to the LIF locus is translocated and cloned as a chromosome insert. In this 10 Mb insert, a 7 Mb extra chromosome region is contained on the telomeric side from the Ig λ gene region, and a 1 Mb extra chromosome region is contained on the centromeric side. In order to first remove the 7 Mb region, chromosome 22 or a modification fragment thereof (a fragment having the loxP sequence inserted into the HCF2 locus and telomeric truncation at the LIF locus) is cleaved at the AP000344 region (I. Dunham et al., Nature 402: 489, 1999) existing very close to the Ig λ gene region and on the telomeric side (about 400 Kb telomeric side) by telomeric truncation (for example, Kuroiwa et al., Nucleic Acid Research, 26: 3447, 1998). Subsequently, the loxP sequence is inserted into the AP000553 region (I. Dunham et al., Nature 402:489, 1999) located very close to the Ig λ gene region and on the centromeric side (about 300 Kb centromeric side) by homologous recombination. These modifications enable translocation and cloning of only an HCF2-Ig λ-AP000344 fragment (about 2.5 Mb) or an AP000553-Ig λ-AP000344 fragment (about 1.5 Mb) to the SC20 chromosome vector as a chromosome insert. The constructed HAC is introduced into a mouse ES cell by a conventional method, and a chimeric mouse can be then produced. After the HAC retention in a chimeric mouse is confirmed, crossing is carried out to obtain an offspring mouse. Confirmation of HAC retention in the resulting offspring mouse enables the judgment of genetic transmission of HAC.

According to the present invention, a transchromosomic non-human animal carrying both of the human antibody heavy chain and λ light chain genes (for example, a mammal such as a mouse) can be efficiently produced through genetic transmission of the total region of the human antibody λ light chain (Ig λ) gene by ΔHAC. This is considered useful as a non-human animal for producing a human antibody which could be a candidate for a pharmaceutical. In human serum, antibodies containing a λ light chain account for about 40% and the number (70) of Vλ gene fragments is roughly equivalent to that (76) of the Vκ chain gene. Thus, an antibody containing the λ chain is considered to significantly contribute to a construction of the diversified human antibody (Popov, A V., J. Exp. Med., 189: 1611, 1999). In contrast, in most humanized antibodies or human antibodies that are currently used as pharmaceuticals in the world the light chain is constituted by the κ light chain. The ΔHAC and the ΔΔHAC transchromosomic mice of the present invention are useful in developing human antibody pharmaceuticals containing the λ light chain. The ΔHAC and the ΔΔHAC transchromosomic mice can genetically transmit chromosome fragments from different species and, thus, mass-production of transchromosomic mice having homogenic traits can be realized by crossing. Further, a mouse carrying a chromosome fragment containing a human antibody κ light chain gene (Tomizuka et al., Proc. Natl. Acad. Sci. USA, vol. 97, 722-727, 2000) or a transgenic mouse containing a human antibody κ light chain gene (Fishwild et al., Nature Biotechnol., 14: 845-851, 1996; Mendez et al., Nature Genet., 15: 146-156, 1997) can be crossed with the ΔHAC or the ΔΔHAC transchromosomic mouse to produce a human antibody-producing mouse which produces a human antibody comprising all of human antibody heavy chain, κ light chain, and λ light chain. There is a report by Nicholson et al. (J. Immunol., 163: 6898, 1999) on a mouse strain which simultaneously expresses a human heavy chain, a κ chain, and a λ chain. They have created a mouse comprising human heavy chain/κ chain and human heavy chain/λ chain molecules as main components for immunoglobulin by a combination between a transgenic mouse having yeast artificial chromosomes (YAC) respectively containing a part of human Ig heavy chain, κ chain, and λ chain introduced therein and an endogenous Ig heavy chain and κ chain knockout mouse. However, diversity and a molecular composition of a human immunoglobulin that is expressed in the mouse strain significantly differ from those in the original human. For example, (i) the human Ig heavy chain YAC consists of only μ and δ constant regions, and another isotype, particularly the Ig γ isotype, which is the largest component, is not expressed in the mouse strain, and (ii) the number of variable regions contained in three types of YACs is small and it is presumed that diversity of human antibodies expressed in the mouse strain is limited.

In the mouse strain simultaneously expressing human Ig heavy chain, κ chain, and λ chain disclosed herein, diversity, molecular composition and the like of the antibody expressed in a human are more faithfully reproduced. For example, since (i) the Ig γ isotypes (all of four subclasses) are expressed and (ii) all variable regions for a heavy chain, a λ chain, and a κ chain are contained, diversity similar to that in a human can be reproduced.

These human antibody-producing transchromosomic mice are immunized with a suitable antigen, and a hybridoma (Ando, Chiba, "Tan-kurohn Koutai Jikken Sousa Nyuumon (Monoclonal Antibody Experimentation and Manipulation Introduction)," Kodansha Scientific, 1991) which is obtained by fusion between a spleen cell and a mouse myeloma is screened by ELISA. Thus, a hybridoma which produces a complete human monoclonal antibody consisting of human immunoglobulin heavy chain and λ light chain can be obtained. These human monoclonal antibodies can be used as pharmaceutical antibodies.

A polyclonal antibody is considered to have greater therapeutic effects than the monoclonal antibody as a therapeutic antibody for treating infectious diseases and the like. Further, a human polyclonal antibody can be also developed as a so-called γ globulin formulation. It was demonstrated that a chimeric mouse can be actually obtained at a high chimerism (about 80% to 100%, preferably about 85% to 100%) from the ES cell retaining the ΔHAC or ΔΔHAC created by the present invention, and that the introduced human artificial chromosome is genetically transmitted with high efficiency and has been continually retained throughout the entire development processes from the state of a fertilized egg until the birth as an offspring mouse. Immunization of a non-human animal such as a mouse with a different species of antigen enables mass-production of antigen-specific human polyclonal antibodies (human λ light chain-containing antibody). This holds expectation as an antibody pharmaceutical which can replace a monoclonal antibody, for which mass-production is difficult.

The human artificial chromosome of the present invention can be introduced into a mouse as well as other non-human animals, for example, mammals, such as rats or pigs. Establishment of the ES cell or the ES-like cell in the animal species other than a mouse is reported in Iannaccone et al., Dev. Biol., 163: 288, 1994 for a rat and in Wheeler et al., Reprod. Fertil. Dev., 6: 563, 1994 for a pig. Further, it has been attempted using cyprinodont, chicken and the like ("Transgenic Animal", Protein Nucleic Acid, Enzyme, October 1995, extra number, KYORITSU SHUPPAN CO., LTD.). Transference of the human artificial chromosome using the ES or ES-like cell as a recipient cell enables the production of the non-human animal which carries a human artificial chromosome or a fragment thereof and expresses the gene on the human artificial chromosome as with the case of a mouse. Further, a human λ light chain-containing antibody can be produced using these non-human animals.

This specification includes part or all of the contents as disclosed in the specification of Japanese Patent Application No. 2001-142371, which is a priority document of the present application.

BEST MODE FOR CARRYING OUT THE INVENTION

The present invention will be described in more detail with reference to the following examples although the present invention is not limited to these examples.

Figure 1:
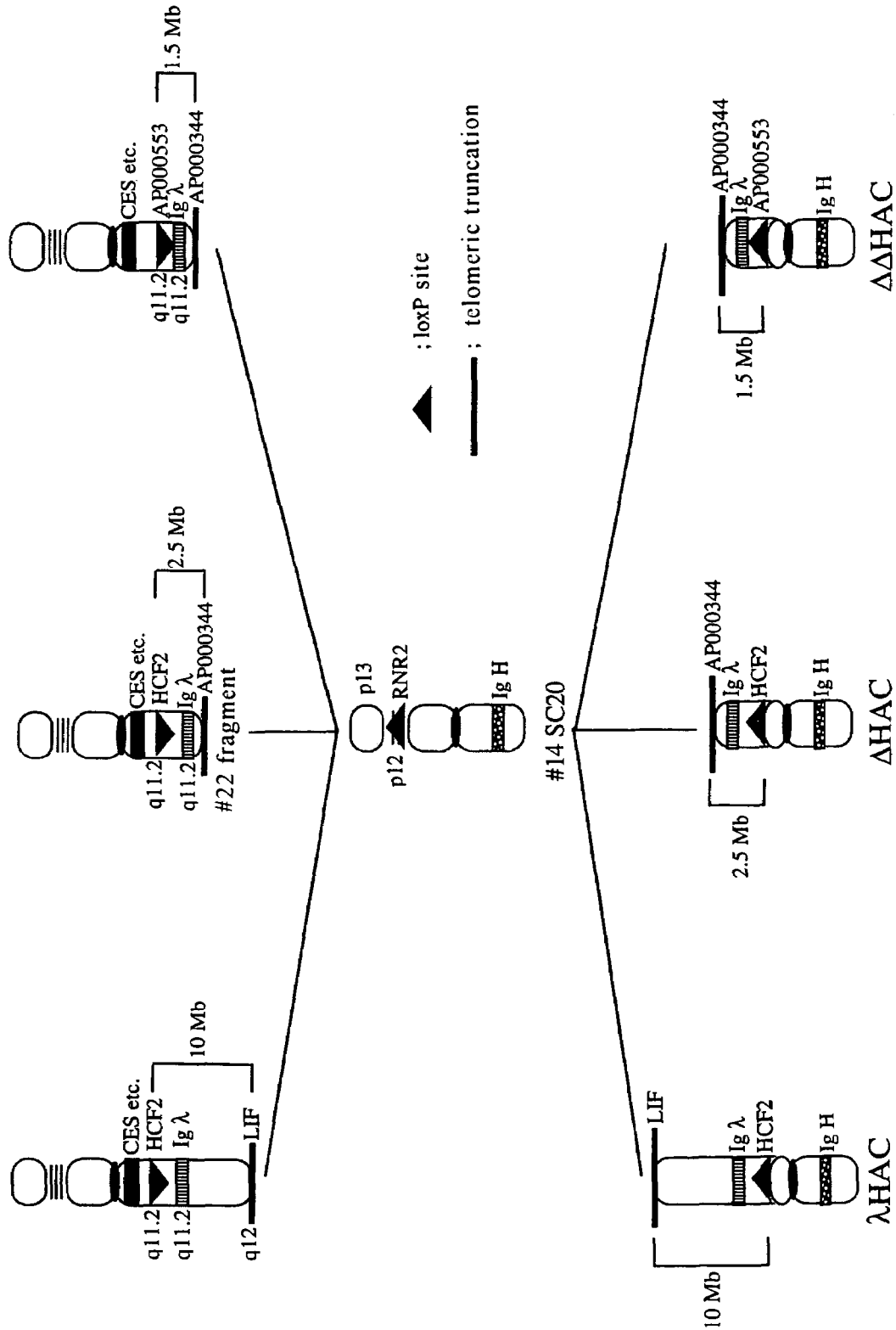
FIG. 1 shows the production of human artificial chromosomes ΔHAC and ΔΔHAC.

The following Example 1 to Example 14 describe the production of human artificial chromosomes ΔHAC and ΔΔHAC, which are prepared by translocating and cloning 2.5 Mb and 1.5 Mb peripheral regions of the antibody λ light chain gene on human chromosome 22 to SC20 chromosome vector (FIG. 1). Further, introduction of each of the produced HACs into an individual mouse and transmission of HAC to an offspring of a chimeric mouse are described.

EXAMPLE 1

Production of Cassette Vector pTELhisD

Figure 2:
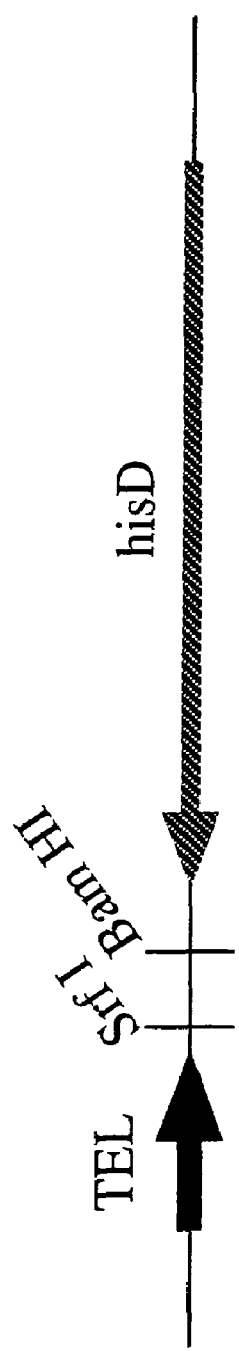
FIG. 2 shows a cassette vector pTELhisD.

A cassette vector pTELPuro (Kuroiwa et al., Nature Biotech., 18: 1086-, 2000) was cleaved with a restriction enzyme NotI (Boehringer) and blunt-ended using the DNA Blunting kit (Toyobo Co., Ltd.) at 72° C. for 5 minutes. After blunting, bacteria-derived alkaline phosphatase (Takara Shuzo Co., Ltd.) was used for dephosphorylation at 65° C. for 1 hour. Thereafter, a restriction enzyme BglII linker (Takara Shuzo Co., Ltd.) was added, and a ligation kit (Takara Shuzo Co., Ltd.) was used to perform ligation. Thus, plasmid pTELBg was produced in which PGKPuro cassette in pTELPuro plasmid was substituted with the BglII linker. This plasmid was cleaved with a restriction enzyme BglII and dephosphorylated in the same manner. Thereafter, it was purified by gel filtration using CHROMA SPIN-TE 400 (Clontech). Subsequently, a hisD fragment, which was cleaved out from plasmid #1-132 (distributed by Professor Shun-ichi Takeda, Kyoto University) with a restriction enzyme BamHI, was added to perform a ligation reaction in the same manner. Thus, a cassette vector pTELhisD was produced in which the PGKPuro cassette in the pTELPuro plasmid was substituted with the hisD cassette (FIG. 2).

EXAMPLE 2

Production of Targeting Vector pTELhisDλI

A targeting vector pTELhisDλI for inserting a human telomeric sequence into the AP000344 region located very close to the Ig λ locus on human chromosome 22 and on the telomeric side (about 400 Kb telomeric side) was produced in the following manner. At the outset, the AP000344 genomic region was amplified by PCR using the primers below.

```
1269D1-F;                                    (SEQ ID NO:1)
5'-TCGAGGATCCGACAAGTTCTCTTCTCTTTTCCTTCTGCCC-3'

1269D1-R;                                    (SEQ ID NO:2)
5'-TCGAGGATCCGCTGCTAAGCTACTGTTCTCTTTTTTCCCC-3'
```

Figure 3:
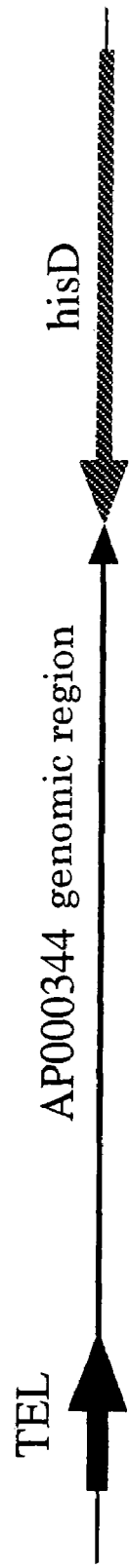
FIG. 3 shows a targeting vector pTELhisDλI.

PCR was carried out using GeneAmp 9600 (manufactured by Perkin-Elmer) as a thermal cycler and LA Taq (Takara Shuzo Co., Ltd.) as the Taq polymerase, and the attached buffer and dNTP (dATP, dCTP, dGTP, dTTP) were used in accordance with the recommended conditions. Regarding the temperature and cycle conditions, after thermal denaturation at 94° C. for 1 minute, 35 cycles of 98° C. for 10 seconds and 68° C. for 11 minutes were carried out. The PCR product was treated with protenase K (Gibco) and then subjected to gel filtration with CHROMA SPIN-TE 400 (Clontech). Thereafter, the PCR product was cleaved with a restriction enzyme BamHI (Boehringer) and then subjected to gel filtration with CHROMA SPIN-TE 1000 (Clontech). This PCR fragment was cloned into the BamHI site of the plasmid pTELhisD. Since the direction of the AP000344 genomic sequence was from centromere to telomere, the cloned AP000344 genomic fragment in the same direction as the human telomere sequence was determined as a targeting vector pTELhisDλI of interest (FIG. 3).

EXAMPLE 3

Production of Targeting Vector p553loxPHyg

A targeting vector p553loxPHyg for inserting loxP sequence which is a recognition sequence of a Cre recombinant enzyme into the AP000553 region located very close to the Ig λ locus on human chromosome 22 and on the centromeric side (about 300 Kb centromeric side) was produced in the following manner. At the outset, the AP000553 genomic region was amplified by PCR using the primers below.

```
553-F3;                                      (SEQ ID NO:3)
5'-TCGAGTCGACTGTAGCTGACTTTAGCCACCCACAAGTAC-3'

553-R3;                                      (SEQ ID NO:4)
5'-TCGAGTCGACCTTGCTGATTATACCTCATCTCCTTCCCTC-3'
```

Figure 4:
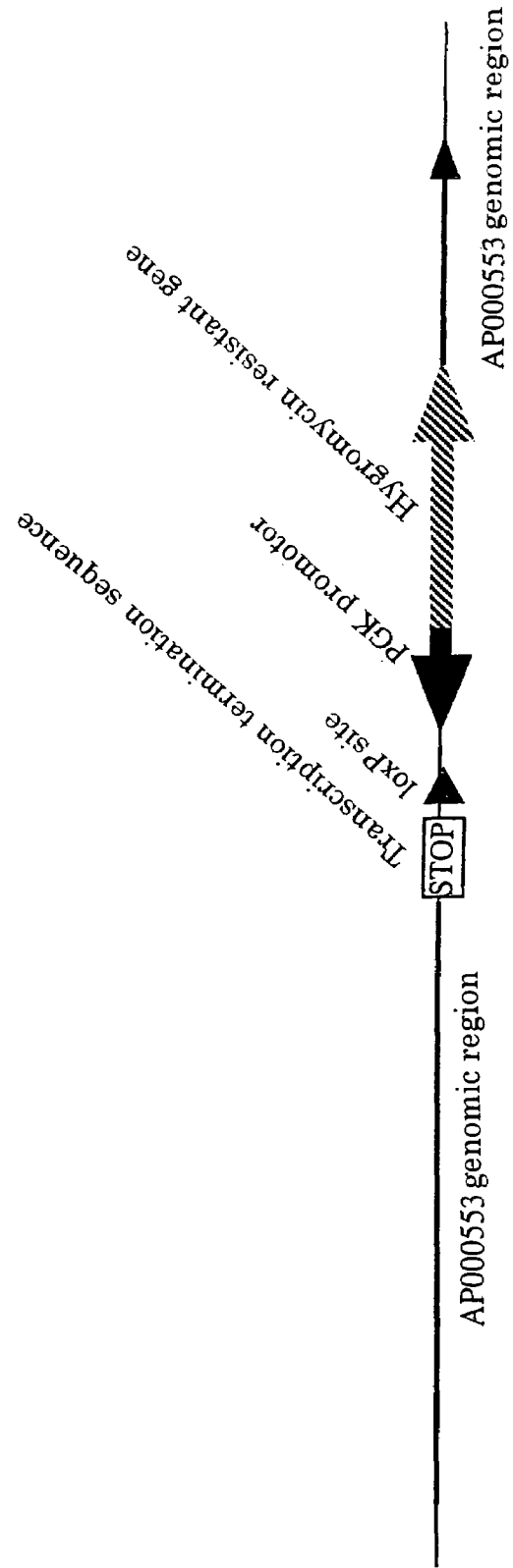
FIG. 4 shows a targeting vector p553loxPHyg.

PCR was carried out using GeneAmp 9600 (manufactured by Perkin-Elmer) as a thermal cycler and LA Taq (Takara Shuzo Co., Ltd.) as the Taq polymerase, and the attached buffer and dNTP (dATP, dCTP, dGTP, dTTP) were used in accordance with the recommended conditions. Regarding the temperature and cycle conditions, after thermal denaturation at 94° C. for 1 minute, 35 cycles of 98° C. for 10 seconds and 68° C. for 15 minutes were carried out. The PCR product was treated with protenase K (Gibco) and then subjected to gel filtration with CHROMA SPIN-TE 400 (Clontech). Thereafter, the PCR product was cleaved with a restriction enzyme SalI (Boehringer) and then subjected to gel filtration with CHROMA SPIN-TE 1000 (Clontech). This PCR fragment was cloned into the SalI site of plasmid pBluescriptII (the NotI site was previously deleted and then the SrfI linker was inserted into the SacII site) (pBS553). Subsequently, pBS553 was cleaved with a restriction enzyme HpaI (Boehringer) and dephosphorylated, and the NotI linker was then inserted by ligation (pBS553N). After pBS553N was cleaved with a restriction enzyme NotI and dephosphorylated, a DNA fragment containing loxP was cleaved out with a restriction enzyme NotI (Boehringer) from a cassette vector ploxPHyg, followed by ligation. A vector having the loxP sequence in the same direction as the cloned AP000553 genomic fragment was determined as a targeting vector p553loxPHyg (FIG. 4).

EXAMPLE 4

Site-Specific Cleavage of Human Chromosome 22 in Chicken DT-40 Cell

The targeting vector pTELhisDλI produced in Example 2 was transfected into the chicken DT-40 cell (clone 52-18) retaining a full length of human chromosome 22 produced by the method described in WO 98/37757 and the DT-40 cell (clone HF38) retaining a fragment of human chromosome 22 that was already cleaved at the LIF locus, and the human telomeric sequence was inserted into the AP000344 genomic region to attempt the cleavage of chromosome 22 at the insertion site.

The chicken DT-40 cell was cultured in RPMI 1640 medium (Gibco) comprising 10% fetal bovine serum (Gibco, hereinafter referred to as "FBS"), 1% chicken serum (Gibco), and $10^{-4}$M 2-nercaptoethanol (Sigma) added therein. About $10^7$ cells were washed once with additive-free RPMI 1640 medium and suspended in 0.5 ml of additive-free RPMI 1640 medium. 25 to 30 µg of targeting vector pTELhisDλI, which has been linearized with a restriction enzyme SrfI (Toyobo Co., Ltd.), was added, transferred into a cuvette (Bio-Rad) for electroporation, and allowed to stand at room temperature for 10 minutes. The cuvette was set in a Gene Pulser (Bio-Rad), and voltage was applied at 550 V, 25 µF. After the cuvette was allowed to stand at room temperature for 10 minutes, it was cultured for 24 hours. Twenty four hours later, the medium was exchanged with a medium containing histidinol (0.5 mg/ml), the culture solution was fractionated to ten 96-well culture plates, and selective culture was carried out for about 2 weeks. Genomic DNA was extracted from a histidinol-resistant clone using the Puregene DNA Isolation Kit (CentraSystem), and cleavage of human chromosome 22 in the AP000344 genomic region was confirmed by PCR using primers for detecting HCF2 (Kuroiwa et al., Nature Biotech. 18: 1086, 2000), Igλ (Tomizuka et al., Nature Genet., 16: 133, 1997), D22S1174, D22S315, D22S275 (BIOS), and LIF (Kuroiwa et al., Nucleic Acid Research, 26: 3447-3448, 1998).

PCR was carried out using GeneAmp 9600 (manufactured by Perkin-Elmer) as a thermal cycler and LA Taq (Takara Shuzo Co., Ltd.) as the Taq polymerase, and the attached buffer and dNTP (dATP, dCTP, dGTP, dTTP) were used in accordance with the recommended conditions. Regarding the temperature and cycle conditions, after thermal denaturation at 94° C. for 1 minute, 35 cycles of 98° C. for 10 seconds, 56° C. for 30 seconds, and 72° C. for 30 seconds were carried out. When clone 52-18 was transfected, 48 clones were screened and 1 clone (T32) was found to be a clone of interest. When HF38 was transfected, 96 clones were screened and 2 clones (HT69, HT72) were found to be clones of interest.

Further, whether chromosome 22 was cleaved in the AP000344 region or not was confirmed by FISH analysis.

In order to visually judge that human chromosome 22 was cleaved in the AP000344 genomic region, FISH analysis was carried out using a probe capable of detecting a hisD resistant gene in a targeting vector. The method was in accordance with Kuroiwa et al. (Nucleic Acid Research, 26: 3447-3448, 1998). Based on COT1 staining (rhodamine label, red), chromosome 22 was found to be fragmented in T32, HT69, and HT72 compared to a full-length human chromosome 22. Further, a signal (FITC label, yellow) derived from a hisD probe was detected at the telomeric end. This indicates that AP000344 into which a targeting vector had been inserted is the telomeric end of a fragment of chromosome 22.

From the above result, it was concluded for T32, HT69, and HT72 that human chromosome 22 was cleaved in the AP000344 region.

EXAMPLE 5

Site-Specific Insertion of loxPHyg Cassette on Human Chromosome 22 in Chicken DT-40 Cell In the above HT69 and 72, the loxP sequence is already inserted into the HCF2 locus (about 1 Mb centromeric side from the Ig λ locus). Therefore, in clone T32, the targeting vector p553loxPHyg produced in Example 3 was transfected into the AP000553 region located very close to the Ig λ locus and on the centromeric side (about 300 Kb centromeric side) to attempt the insertion of the loxP sequence.

In the same manner as described above, a targeting vector p553loxPHyg, which has been linearized with a restriction enzyme SrfI (Toyobo Co., Ltd.), was transfected into clone T32 and selective culture was conducted in a medium containing hygromycin B (1 mg/ml) for about 2 weeks. Genomic DNA was extracted from a hygromycin B-resistant clone and a homologous recombinant was identified by PCR using the 2 sets of primers below.

```
553-F4;
5'-GCTAAGGCACTTCGGTTCTCTTTGTGTTC-3'   (SEQ ID NO:5)

553-R4;
5'-GGTTGTCTTTAAAAGCAGGGATAAGGATG-3'   (SEQ ID NO:6)

553-F5;
5'-AGAAGAAAGGAGTGGGTGCTAAACATTCAG-3'  (SEQ ID NO:7)

553-R5;
5'-GGTTAGATGGCACCAAATGAAAGGAGAAG-3'   (SEQ ID NO:8)
```

PCR was carried out using GeneAmp 9600 (manufactured by Perkin-Elmer) as a thermal cycler and LA Taq (Takara Shuzo Co., Ltd.) as the Taq polymerase, and the attached buffer and dNTP (dATP, dCTP, dGTP, dTTP) were used in accordance with the recommended conditions. Regarding the temperature and cycle conditions, after thermal denaturation at 94° C. for 1 minute, 35 cycles of 98° C. for 10 seconds and 68° C. for 15 minutes were carried out. As a result of screening of 69 clones, 3 clones (553-2, 6, 14) were identified as homologous recombinants.

EXAMPLE 6

Construction of Human Artificial Chromosome ΔHAC Prepared by Translocating and Cloning 2.5 Mb Periphery of Human Antibody λ Light Chain Gene Region (HCF2-Ig λ-AP000344) to SC20 Chromosome Vector At the outset, clone HT72 obtained in Example 4 was subjected to cell fusion with clone R of the DT-40 cell retaining the SC20 chromosome vector (Kuroiwa et al., Nature Biotech. 18: 1086, 2000) to produce a DT-40 hybrid retaining both a fragment of human chromosome 22 and an a fragment of chromosome 14 (SC20 chromosome vector).

(1) Production of DT-40 Hybrid Retaining Both a Fragment of Human Chromosome 22 and SC20 Chromosome Vector Clone R was cultured in RPMI 1640 medium containing blasticidin S (10 μg/ml) and clone HT72 was cultured in RPMI 1640 medium containing hygromycin B (1 mg/ml). Both clones were mixed with each other in amounts of 1 to 2×10⁷ respectively and centrifuged, and then washed twice with a serum-free RPMI 1640 medium. After the residual medium was completely removed, 0.5 ml of 50% PEG 1500 (Boehringer), which was preheated at 37° C., was gently added, and the mixture was vigorously mixed using a pipette for about 2 minutes. Thereafter, 1 ml of serum-free RPMI 1640 medium was slowly added over a period of 1 minute, 9 ml of serum-free RPMI 1640 medium was then added over a period of about 3 minutes, and the mixture was allowed to stand at 37° C. for 10 minutes. Thereafter, the mixture was centrifuged at 1,200 rpm for 5 minutes and cultured for 24 to 48 hours in a serum-containing RPMI 1640 medium. Thereafter, the medium was exchanged with RPMI 1640 medium containing blasticidin S (10 μg/ml) and hygromycin B (1 mg/ml), and the culture solution was fractionated to five 24-well culture plates, followed by culturing for 3 to 4 weeks. Genomic DNA was extracted from the double-resistant clone, and PCR was carried out using the primers below to confirm that two fragments, i.e., a fragment of human chromosome 14 (SC20 chromosome vector) and a fragment of chromosome 22, were retained.

Primers for Detecting Human Chromosome 14

```
VH3-F; 5'-AGTGAGATAAGCAGTGGATG-3'   (SEQ ID NO:9)

VH3-R; 5'-GTTGTGCTACTCCCATCACT-3'   (SEQ ID NO:10)
```

Primers for Detecting Human Chromosome 22

```
Igλ-F; 5'-GAGAGTTGCAGAAGGGGTGACT-3'  (SEQ ID NO:11)

Igλ-R; 5'-GGAGACCACCAAACCCTCCAAA-3'  (SEQ ID NO:12)
```

PCR was carried out using GeneAmp 9600 (manufactured by Perkin-Elmer) as a thermal cycler and Ex Taq (Takara Shuzo Co., Ltd.) as the Taq polymerase, and the attached buffer and dNTP (dATP, dCTP, dGTP, dTTP) were used in accordance with the recommended conditions. Regarding the temperature and cycle conditions, after thermal denaturation at 94° C. for 1 minute, 35 cycles of 98° C. for 10 seconds, 56° C. for 30 seconds, and 72° C. for 30 seconds were carried out. As a result of PCR, 6 clones (56HT2, 3, 4, 5, 6, 7) were found positive. Further, the result of FISH analysis using human COT1 DNA as a probe demonstrated that all these clones retained two fragments of human chromosome independently from each other. Based on the above results, these 6 hybrid clones were judged to retain two fragments, i.e., a fragment of human chromosome 14 (SC20 chromosome vector) and a fragment of chromosome 22.

(2) Site-Specific Translocation of 2.5 Mb Region of Human Chromosome 22 (HCF2-Igλ-AP000344) to SC20 Chromosome Vector in DT-40 Hybrid Clone (56HT2)

(2)-1 Construction of Stable Expression Vector for Cre Recombinant Enzyme pBS185Puro In accordance with the method by Kuroiwa et al. (described above), site-specific translocation between human chromosomes was carried out using the Cre-loxP system. Since recombination efficiency between non-homologous chromosomes was expected to be very low even in this system, it was considered that the Cre enzyme should be stably expressed instead of being transiently expressed. Thus, the following type of expression vector was constructed.

A PGKPuro fragment which was cleaved out by EcoRI from a plasmid of which the NotI site in plasmid PGKPuro (distributed by Dr. Peter W. Laird, WHITEHEAD INSTITUTE) had been substituted by the EcoRI site, was cloned into the EcoRI site in a Cre recombinase expression vector: pBS185 (Gibco) (pBS185Puro).

(2)-2 Site-Specific Translocation of 2.5 Mb Region of Human Chromosome 22 (HCF2-Igλ-AP000344) to SC20 Chromosome Vector in DT-40 Hybrid Clone Using Cre-loxP System In the same manner as described above, a stable Cre recombinant enzyme expression vector: pBS185Puro which had been linearized with a restriction enzyme KpnI (Boehringer) was transfected into the 56HT2 hybrid clone, the culture solution was fractionated to a 24-well plate, and selective culture was conducted in the presence of puromycin (3 µg/ml) for about 2 weeks. Genomes were extracted from each well, and nested PCR using the two sets of primers below was carried out to determine whether or not translocation between the SC20 chromosome vector and a fragment of human chromosome 22 had occurred.

```
PGK-1; 5'-ATAGCAGCTTTGCTCCTTCG-3'     (SEQ ID NO:13)

GFP-1; 5'-TTCTCTCCTGCACATAGCCC-3'     (SEQ ID NO:14)

PGK-2; 5'-TGTTCTCCTCTTCCTACTCTCC-3'   (SEQ ID NO:15)

GFP-2; 5'-TGAAGGTAGTGACCAGTGTTGG-3'   (SEQ ID NO:16)
```

PCR was carried out using GeneAmp 9600 (manufactured by Perkin-Elmer) as a thermal cycler and Ex Taq (Takara Shuzo Co., Ltd.) as the Taq polymerase, and the attached buffer and dNTP (dATP, dCTP, dGTP, dTTP) were used in accordance with the recommended conditions. As the first PCR, after thermal denaturation at 94° C. for 1 minute, 35 cycles of 98° C. for 10 seconds, 61° C. for 30 seconds, and 72° C. for 1 minute were carried out using PGK-1 and GFP-1 as primers. Using a part of this reaction solution as a template, 35 cycles of 98° C. for 10 seconds, 59° C. for 30 seconds, and 72° C. for 30 seconds were then carried out using PGK-2 and GFP-2 as primers. A cell pool in a well which found by PCR to be translocated was cultured until the cell number reached $10^7$, and the pool was suspended in 4 ml of PBS (phosphate buffered saline solution) having 5% FBS and 1 µg/ml propidium iodide (PI) added therein and analyzed by FACS Vantage (Becton Dickinson). As reported by Kuroiwa et al. (described above), when recombination or translocation between loxPs occurred, the GFP gene is reconstructed and expressed. Thus, translocated cells can be detected by FACS. Sorting of cell fractions which were considered to be GFP positive was repeated twice. Culture after every sorting operation was performed in RPMI 1640 medium containing hygromycin B (1 mg/ml). As a result, GFP positive cells were concentrated at a purity of 98 to 99%.

Subsequently, whether or not recombination between loxPs in GFP positive clone (ΔH21), which was cloned by FACS, had occurred as expected was confirmed by PCR using PGK-2 and GFP-2 as primers. Further, clone ΔH21 was subjected to FISH analysis (Kuroiwa et al., described above) using a human chromosome 14-specific probe (rhodamine label) and a human chromosome 22-specific probe (FITC label). As a result, the existence of an artificial chromosome in which the human chromosome 22 region was clearly translocated to the SC20 chromosome vector (a fragment of human chromosome 14) was confirmed.

Based on the above result, it was concluded for clone ΔH21 that a human artificial chromosome ΔHAC was constructed in which 2.5 Mb of periphery of human antibody λ light chain gene region (HCF2-Igλ-AP000344) was translocated and cloned to the SC20 chromosome vector.

A chicken DT-40 cell (ΔHAC) retaining ΔHAC was deposited internationally at the International Patent Organism. Depositary of the National Institute of Advanced Industrial Science and Technology (Tsukuba Central 6, 1-1-1 Higashi, Tsukuba, Ibaraki, Japan) as of May 9, 2001, under the accession number of FERM-BP-7582.

EXAMPLE 7

Construction of Human Artificial Chromosome ΔΔHAC Prepared by translocating and Cloning 1.5 Mb Periphery of Human Antibody λ Light Chain Gene Region (AP000553-Igλ-AP000344) to SC20 Chromosome Vector In the above ΔHAC, about 1 Mb of extra region still remains between Ig λ and HCF2. For the purpose of strictly removing an extra chromosome region and translocating and cloning only the periphery of an Ig λ gene region, it was attempted to construct human artificial chromosome ΔΔHAC in which 1.5 Mb of AP000553-Igλ-AP000344 region was translocated and cloned to the SC20 chromosome vector.

At the outset, clone 553-2 obtained in Example 5 was subjected to cell fusion with the clone R to produce the DT-40 hybrid retaining both the fragment of human chromosome 22 and chromosome 14 (SC20 chromosome vector).

(1) Production of DT-40 Hybrid Retaining Both the Fragment of Human Chromosome 22 and SC20 Chromosome Vector The clone R was cultured in RPMI 1640 medium containing blasticidin S (10 µg/ml) and the clone 553-2 was cultured in RPMI 1640 medium containing hygromycin B (1 mg/ml). Both clones were mixed with each other in amounts of 1 to $2\times10^7$, respectively and centrifuged, and then washed twice with a serum-free RPMI 1640 medium. After the residual medium was completely removed, 0.5 ml of 50% PEG 1500 (Boehringer), which was preheated at 37° C., was gently added, and the mixture was vigorously mixed using a pipette for about 2 minutes. Thereafter, 1 ml of serum-free RPMI 1640 medium was slowly added over a period of 1 minute, 9 ml of serum-free RPMI 1640 medium was then added over a period of about 3 minutes, and the mixture was allowed to stand at 37° C. for 10 minutes. Thereafter, the mixture was centrifuged at 1,200 rpm for 5 minutes and cultured for 24 to 48 hours in a serum-containing RPMI 1640 medium. Thereafter, the medium was exchanged with RPMI 1640 medium containing blasticidin S (10 µg/ml) and hygromycin B (1 mg/ml), and the culture solution was fractionated to five 24-well culture plates, followed by culturing for 3 to 4 weeks. Genomic DNA was extracted from an obtained hybrid clone (for example, clone 553R1), and PCR was carried out using the same primers as used in Example 6 to confirm that two fragments, i.e., the fragment of human chromosome 14 and the fragment of chromosome 22, were retained. Further, FISH analysis was carried out using human COT1 DNA as a probe and two fragments of human chromosome were confirmed to exist independently from each other. Based on the above experiment, it was concluded that hybrid clone 553R1 retained two fragments, i.e., the fragment of human chromosome 14 (SC20 chromosome vector) and the fragment of chromosome 22.

(2) Site-Specific Translocation of 1.5 Mb Region of Human Chromosome 22 (AP000553-Igλ-AP000344) to SC20 Chromosome Vector in DT-40 Hybrid Clone (553R1)

In the same manner as described above, a stable Cre recombinant enzyme expression vector: pBS185Puro which had been linearized with a restriction enzyme KpnI (Boehringer) was transfected into the hybrid clone 553R1, the culture solution was fractionated to a 12-well plate, and selective culture was conducted in the presence of puromycin (3 µg/ml) for about 2 weeks. Genomes were extracted from each well, and nested PCR using the two sets of primers below was carried out to determine whether or not translocation between the SC20 chromosome vector and a fragment of human chromosome 22 had occurred.

```
PGK-1; 5'-ATAGCAGCTTTGCTCCTTCG-3'      (SEQ ID NO:13)
GFP-1; 5'-TTCTCTCCTGCACATAGCCC-3'      (SEQ ID NO:14)
PGK-2; 5'-TGTTCTCCTCTTCCTACTCTCC-3'    (SEQ ID NO:15)
GFP-2; 5'-TGAAGGTAGTGACCAGTGTTGG-3'    (SEQ ID NO:16)
```

PCR was carried out using GeneAmp 9600 (manufactured by Perkin-Elmer) as a thermal cycler and Ex Taq (Takara Shuzo Co., Ltd.) as the Taq polymerase, and the attached buffer and dNTP (dATP, dCTP, dGTP, dTTP) were used in accordance with the recommended conditions. As the first PCR, after thermal denaturation at 94° C. for 1 minute, 35 cycles of 98° C. for 10 seconds, 61° C. for 30 seconds, and 72° C. for 1 minute were carried out using PGK-1 and GFP-1 as primers. Using a part of this reaction solution as a template, 35 cycles of 98° C. for 10 seconds, 59° C. for 30 seconds, and 72° C. for 30 seconds were carried out using PGK-2 and GFP-2 as primers. Cell pools (2 pools: DDH5, 6) in a well which were found by PCR to be translocated increased until the cell number reached $10^7$, and the pool was suspended in 4 ml of PBS (phosphate buffered saline solution) having 5% FBS and 1 µg/ml propidium iodide (PI) added therein and analyzed by FACS Vantage (Becton Dickinson). Sorting of cell fractions which were considered to be GFP positive was repeated twice. Culture after every sorting operation was performed in RPMI 1640 medium containing hygromycin B (1 mg/ml). As a result, GFP positive cells were concentrated at a purity of 98 to 99%.

Subsequently, whether or not recombination between loxPs in GFP positive clones (ΔΔH5, 6), which were cloned by FACS, had occurred as expected was confirmed by PCR using PGK-2 and GFP-2 as primers. Further, clones ΔΔH5, 6 were subjected to FISH analysis (Kuroiwa et al., described above) using a human chromosome 14-specific probe (rhodamine label) and a human chromosome 22-specific probe (FITC label). As a result, the existence of an artificial chromosome in which a region of human chromosome 22 was clearly translocated to the SC20 chromosome vector (a fragment of human chromosome 14) was confirmed for both clones.

Based on the above result, it was concluded for the two clones ΔΔH5, 6 that human artificial chromosome ΔΔHAC was constructed in which 1.5 Mb periphery of human antibody λ light chain gene region (AP000553-Igλ-AP000344) was translocated and cloned to the SC20 chromosome vector.

A chicken DT-40 cell (ΔΔHAC) retaining ΔΔHAC was deposited internationally at the International Patent Organism Depositary of the National Institute of Advanced Industrial Science and Technology (Tsukuba Central 6, 1-1-1 Higashi, Tsukuba, Ibaraki, Japan) as of May 9, 2001, under the accession number of FERM-BP-7581.

EXAMPLE 8

Cell Fusion Between ΔHAC-Containing DT-40 Hybrid Cell and Chinese Hamster CHO Cell As reported by Kuroiwa et al. (described above), introduction of a constructed HAC into a CHO cell was first attempted to introduce a constructed HAC into a mouse ES cell. However, the ΔHAC-containing DT-40 hybrid cell ΔH21 had a low microcell-forming ability and, thus, introduction of ΔHAC into the CHO cell by a microcell method was not successful (WO 00/10383). Thus, introduction of ΔHAC into the CHO cell through cell fusion between the ΔHAC-containing DT-40hybrid cell ΔH21 and the CHO cell was newly attempted.

1 to $2 \times 10^7$ ΔH21 clones and $1 \times 10^7$ CHO cells were mixed and centrifuged, and the mixture was then washed twice with a serum-free DMEM medium. After the residual medium was completely removed, 0.5 ml of 50% PEG 1500 (Boehringer), which was preheated at 37° C., was gently added, and the mixture was vigorously mixed using a pipette for about 2 minutes. Thereafter, 1 ml of serum-free DMEM medium was slowly added over a period of 1 minute, 9 ml of serum-free DMEM medium was then added over a period of about 3 minutes, and the mixture was allowed to stand at 37° C. for 10 minutes. Thereafter, the mixture was centrifuged at 1,200 rpm for 5 minutes and cultured in a serum-containing F12 medium (Gibco) for 24 hours. Thereafter, the medium was exchanged with a f12 medium containing G418 (1 mg/ml) and hygromycin B (0.6 mg/ml), and the culture solution was fractionated to three 24-well culture plates, followed by culturing for 3 to 4 weeks.

Genomes were extracted from the resistant clone, and PCR was carried out using primers for detecting VH3 and Ig λ in the same manner as in Example 6. As a result, 2 clones (D15, ΔC30) were found PCR positive. Further, these 2 clones were subjected to FISH analysis by double staining using a human chromosome 14-specific probe and a human chromosome 22-specific probe in the same manner as in Example 6 to confirm the existence of ΔHAC. Regarding cell fusion between DT-40 and CHO, most of chromosomes derived from DT-40 were dropped out and the karyotype was substantially the same as that of the wild-type CHO cell. This eventually enabled the production of the CHO clone retaining ΔHAC through cell fusion between the DT-40 cell and the CHO cell. This indicated the possibility that the cell fusion might be useful as an alternative method for the case where the microcell-forming ability of DT-40 clone was low.

EXAMPLE 9

Introduction of ΔΔHAC from ΔΔHAC-Containing DT-40 Hybrid Cell into CHO Cell

The microcell-forming ability of ΔΔHAC-containing DT-40 hybrid clones ΔΔH5, 6 was not insufficient and, thus, the microcell method was employed as reported by Kuroiwa et al. (described above).

DT-40 hybrid clones ΔΔH5, 6 were respectively cultured in eight T225 flasks (Sumiron), and the medium was exchanged with RPMI 1640 medium having 20% FBS, 1% chicken serum, $10^{-4}$ M 2-mercaptoethanol, and 0.05 µg/ml colcemid added therein when the content of the flasks became confluent. Cells were cultured for an additional 24 hours to form microcells. The cells were suspended in 24 ml of serum RPMI 1640 medium, fractionated in an amount of 2 ml each to twelve 25 $cm^2$ flasks for centrifugation (Corning) which were precoated with 100 µg/ml poly L-ysin, and cultured at 37° C. for 1 hour. The cells were then allowed to adhere on the bottoms of the flasks. The culture solution was removed, and a solution of cytochalasin B (10 µg/ml, Sigma), which was preheated at 37° C., was filled into a flask for centrifugation and subjected to centrifugation at 34° C. at 8,000 rpm for 1 hour. Microcells were suspended in a serum-free DMEM medium and purified through 8 µm, 5 µm, and 3 µm filters. After purification, the microcells were centrifuged at 1,700 rpm for 10 minutes and suspended in 5 ml of serum-free DMEM medium. Separately, about $10^7$ CHO cells were peeled by trypsin treatment, washed twice with serum-free DMEM medium, and suspended in 5 ml of serum-free DMEM medium. The microcells were recentrifuged at 1,700 rpm for 10 minutes, and 5 ml of the above CHO suspension was gently superposed thereon without removing the supernatant. After centrifugation, the culture solution was removed, 0.5 ml of PEG 1500 solution (Boehringer) was added, and the mixture was vigorously stirred using a pipette for about 2 minutes. Thereafter, 10 ml of serum-free DMEM medium was slowly added over a period of about 3 minutes and the mixture was allowed to stand at 37° C. for 10 minutes. After centrifugation, cells were suspended in F12 medium containing 10% FBS (Gibco) and fractionated to five to six 24-well culture plates, followed by culturing at 37° C. for 24 hours. Thereafter, the medium was exchanged with the F12 medium containing 800 µg/ml G418 and selective culture was conducted for 3 to 4 weeks.

Genomic DNA was extracted from the G418-resistant clone, and PCR was carried out using primers for detecting Ig λ and VH3 and PGK-2 and GFP-2 primers under the same conditions as described above to identify a CHO clone retaining ΔΔHAC (for example, ΔΔC10, 13). Further, the clones which were found positive by PCR were subjected to FISH analysis using a human chromosome 14-specific probe and a human chromosome 22-specific probe to visually confirm the existence of ΔΔHAC. Based on these results, it was concluded that the clones of CHO cell retaining ΔΔHAC were obtained.

EXAMPLE 10

Introduction of ΔHAC or ΔΔHAC from CHO Cell into Mouse ES Cell

In order to produce a chimeric mouse carrying ΔHAC or ΔΔHAC, ΔHAC or ΔΔHAC was transduced from the CHO cell retaining ΔHAC or ΔΔHAC obtained in Examples 8 or 9 to the mouse ES cell (wild-type TT2F) by the microcell method.

In accordance with the method by Tomizuka et al. (Nature Genet. 16: 133, 1997), microcells were purified from the CHO cells (D15, ΔΔC 10, ΔΔC13 or the like) retaining about $10^8$ ΔHAC or ΔΔHAC and suspended in 5 ml of DMEM. About $10^7$ mouse ES cells TT2F were peeled by trypsin treatment, washed three times with DMEM, suspended in 5 ml of DMEM, added to the centrifuged microcells, and centrifuged at 1,250 rpm for 10 minutes. The supernatant was then completely removed. The precipitate was thoroughly loosened by tapping, 0.5 ml of 1:1.4 PEG solution [a solution of 5 g PEG 1000 (Wako Pure Chemicals Industries Ltd.) and 1 ml of DMSO (Sigma) in 6 ml of DMEM] was added, and the mixture was thoroughly stirred for about 1 minute and 30 seconds. Thereafter, 10 ml of DMEM was slowly added, the mixture was centrifuged at 1,250 rpm for 10 minutes and suspended in 30 ml of ES medium and fractionated to three petri dishes (Corning, diameter 100 mm) previously loaded with feeder cells, followed by culturing. The medium was exchanged with a medium containing 300 µg/ml G418 twenty-four hours later, and selective culture was conducted for about 1 week.

As a result, 14 clones were found positive from among D15 clones (retaining ΔHAC), 8 clones from among ΔΔC10 (retaining ΔΔHAC), and 8 clones from among ΔΔC13 (retaining ΔΔHAC) by PCR using primers for detecting Ig λ and VH3. Further, as a result of FISH analysis using human COT1 DNA probe (Tomizuka et al., Nature Genet. 16: 133, 1997), the existence of ΔHAC or ΔΔHAC specifically detected by the COT1 probe was confirmed.

Based on the above results, it was concluded that 14 clones were obtained from ΔHAC-retaining TT2F cells and 16 clones from ΔΔHAC-retaining TT2F cells.

EXAMPLE 11

Production of Chimeric Mouse Carrying Human Artificial Chromosomes ΔHAC and ΔΔHAC A chimeric mouse was produced in accordance with the method by Tomizuka et al. (Nature Genet., 16: 133, 1997) using clones of the ES cell obtained in Example 10. As a host, MCH(ICR) (white, purchased from CLEA Japan, Inc.) or a 8-cell stage embryo obtained by female-male crossing of antibody heavy chain knock-out mice (Tomizuka et al., Proc. Natl. Acad. Sci. USA, vol. 97, 722-727, 2000) was used. Whether an offspring mouse obtained by transplanting the injected embryo into the foster parent is chimeric or not can be determined based on its coat color. Wild-type TT2F/ΔHAC clones (TΔ#6, obtained in Example 10) were injected into 400 embryos and the injected embryos were transplanted into foster parents. As a result, 7 chimeric mice (a dark brown portion is recognized in coat color) were borne. More specifically, it was shown that the ES cell strain (TT2F) retaining human artificial chromosome ΔHAC has a chimera-forming ability, that is, has an ability to differentiate into normal tissues of an individual mouse.

In the same manner as described above, wild-type TT2F/ΔΔHAC clones (TΔΔ#21) obtained in Example 10 were injected into 180 embryos and the injected embryos were transplanted into the foster parents. As a result, 2 chimeric mice (a dark brown portion is recognized in coat color) were borne. One of them was an individual with a chimerism of about 100%, i.e., a white portion could not be substantially observed. More specifically, it was shown that the ES cell strain (TT2F) retaining human artificial chromosome ΔΔHAC has a chimera-forming ability, that is, has an ability to differentiate into normal tissues of an individual mouse.

EXAMPLE 12

Retention of Artificial Chromosome in Somatic Cell of Chimeric Mouse Produced from ES Cell Retaining Human Artificial Chromosomes ΔHAC and ΔΔHAC Genomic DNA was prepared from a tail of the chimeric mouse produced in Example 11 from TT2F/ΔHAC clone (TΔ#6) (chimerism of about 85%) by the method reported by Tomizuka et al. (Nature Genet., 16: 133, 1997), and PCR was carried out using primers for detecting Ig λ and VH3 in the same manner as described above to examine ΔHAC retention. As a result, it was found to be positive for both of the primers and ΔHAC retention in the somatic cells of the chimeric mouse was confirmed. Serum was collected from a chimeric mouse (a chimerism of about 85%) and another chimeric mouse produced from TΔ#6 (a chimerism of about 90%), and the expression of human μ chain and human λ chain proteins was examined by ELISA (Tomizuka et al., Nature Genet., 16: 133, 1997, Proc. Natl. Acad. Sci, USA, vol. 97, 722-727, 2000). As a result, human μ chain and λ chain were both positive for both of the chimeric mice.

Similarly, DNA, derived from a tail of the chimeric mouse (a chimerism of about 100%, Example 11) derived. from the ES cell clone (TΔΔ#21) retaining ΔΔHAC, was found positive for the above two primers and ΔΔHAC retention was confirmed. Further, ELISA analysis similar to the above indicates that both human μ chain and λ chain are positive in serum of the ΔΔHAC-carrying chimeric mouse.

The chimerism of the λHAC carrying chimeric mouse obtained from the ES cell retaining λHAC was about 80% at the maximum, however, chimeric mice with chimerisms of about 85% and 90% were obtained from ΔHAC and a chimeric mouse with a chimerism of about 100% was obtained from ΔΔHAC. Use of a chimeric mouse with a higher chimerism can result in differentiation of introduced chromosome retaining ES cell into germ cells with higher efficiency and genetic transmission of the introduced chromosome. That is, use of ΔHAC and ΔΔHAC can be expected to enhance the genetic transmission efficiency of a fragment of human chromosome 22 containing an antibody immunoglobulin λ chain gene in a mouse.

EXAMPLE 13

Genetic Transmission of Artificial Chromosome from Chimeric Mouse Carrying Human Artificial Chromosome ΔHAC and ΔΔHAC A chimeric female mouse (chimerism of about 85%) produced in Example 11 from TT2F/ΔHAC clone (TΔ#6) was crossed with a male mouse MCH(ICR) (white, purchased from CLEA Japan, Inc.). Among 10 offspring mice born from the chimeric mouse, 4 had a coat color of dark brown, which indicates the retention of a dominant genotype derived from the ES cell. That is, the ES cell strain and TΔ#6 retaining ΔHAC were found to be differentiated into functional egg cells in a chimeric female mouse. A part of the tails of the four dark brown offspring mice was cut out and genomic DNA was prepared from the sample. The obtained DNA was subjected to PCR using primers for detecting Ig λ and VH3 in the same manner as described above. As a result of the examination on ΔHAC retention, all of the four mice were found positive for both of the primers and ΔHAC retention in the offspring of the chimeric mouse was confirmed. Further, serum was collected from 3 out of the 4 mice and expression of human μ chain and human λ chain was examined by ELISA (Tomizuka et al., Nature Genet., 16: 133, 1997, Proc. Natl. Acad. Sci. USA., vol. 97, 722-727, 2000). As a result, all the examined three mice were found positive for both human μ chain and λ chain. Genetic transmission of ΔΔHAC from the chimeric mouse produced from clone TT2F/ΔΔHAC in Example 11 is indicated in the same manner.

In mouse lineages that respectively carry and genetically transmit either ΔHAC or ΔΔHAC, stable retention of each HAC is examined by FISH analysis and the like of fibroblasts prepared from tails. As a result, stable retention of each HAC in the somatic cell of the mouse lineage is shown.

In mouse lineages that carry and genetically transmit either ΔHAC or ΔΔHAC, expression of complete human antibody molecules consisting of human Ig λ chain/heavy chain is confirmed by ELISA and the like. Further, a mouse lineage that respectively carries and genetically transmits either ΔHAC or ΔΔHAC is repetitively crossed with a mouse lineage having deleted endogenous antibody heavy chain and light chain κ gene, thereby obtaining mouse lineages carrying each HAC and being homogeneous in terms of the endogenous antibody heavy chain and κ chain genes deficiency. These mouse lineages mainly produce a complete human antibody comprising the human Ig heavy chain and λ chain.

EXAMPLE 14

Construction of Mouse Lineage Simultaneously Expressing Human Immunoglobulin Heavy Chain, Light Chain λ, and Light Chain κ

A mouse lineage which simultaneously produces the human Ig heavy chain, κ light chain, and λ light chain and produces an antibody mainly composed of a molecule comprising the human Ig heavy chain and κ light chain or λ light chain can be produced by crossing between the lineage (A) and lineage (B) below.

(A) TC (ΔHAC), a mouse lineage which carries and genetically transmits ΔHAC, or TC (ΔΔHAC), a mouse lineage which carries and genetically transmits ΔHAC (see Example 13).

(B) TC(W23)/ΔH/Δκ, a mouse lineage which is a homozygote for the endogenous antibody heavy chain and κ chain genes deficiency and carries and genetically transmits fragment W23 of chromosome 2 (Tomizuka et al., Proc. Natl. Acad. Sci. USA., vol. 97, 722-727, 2000).

The offspring mice obtained by crossing between lineage (A) and lineage (B) are analyzed by the method described in Example 13 and the report by Tomizuka et al. (Proc. Natl. Acad. Sci. USA., vol. 97, 722-727, 2000). All the offspring mice obtained by this crossing are heterozygotes for the endogenous antibody heavy chain deficiency and κ chain deficiency, and individuals carrying ΔHAC (or ΔΔHAC) and individuals carrying fragment W23 are selected therefrom and crossed with further obtain offsprings. Individuals (lineage (D)) which are homozygotes for the endogenous antibody heavy chain deficiency and the κ chain deficiency and simultaneously carry ΔHAC (or ΔΔHAC) and fragment W23 are finally selected.

In lineage (D), expression of the human immunoglobulin heavy chain, κ chain, and λ chain are confirmed by the method described in the report by Tomizuka et al. (Proc. Natl. Acad. Sci. USA., vol. 97, 722-727, 2000) and (WO 98/37757).

EXAMPLE 15

Construction of Mouse Lineage Carrying ΔHAC and Having Alleles of Both Endogenous Ig Heavy Chain and κ Chain Genes Destructed TC (ΔHAC) produced in Example 13 was back crossed with the endogenous Ig heavy chain and κ chain knock-out mouse lineage described in the report by Tomizuka et al. (Proc. Natl. Acad. Sci. USA., vol. 97, 722-727, 2000). The obtained individual mice were analyzed for the genotype by PCR and ELISA (see Example 12 and the report by Tomizuka et al.).

As a result, individuals which carried ΔHAC and were homozygotes for the endogenous Ig heavy chain knock-out and were homozygotes for the endogenous Igκ chain knock-out were obtained (hereinafter referred to as "TC(ΔHAC)/ΔH/Δκ").

In serum of two TC(ΔHAC)/ΔH/Δκ individuals (8-week old), expression of the human Ig heavy chain and λ chain proteins was analyzed by ELISA described in the report by Kuroiwa et al. (Nature Biotechnol., 18: 1086-, 2000). As a result, the expression level in each mouse was as follows: human Ig μ chain: 430 μg/ml, Ig γ chain: 180 μg/ml, Ig λ chain: 330 μg/ml; and human Ig μ chain: 720 μg/ml, Ig γ chain: 320 μg/ml, Ig λ chain: 520 μg/ml.

EXAMPLE 16

Construction of Mouse Lineage Carrying a Fragment of Human Chromosome 2 Containing ΔHAC and Human Ig κ Chain Gene and Having Alleles of Both Endogenous Ig Heavy Chain and κ Chain Genes Destructed Individual mice obtained by crossing between a mouse lineage carrying a fragment of human chromosome 2 (hCF (W23)) containing the human Ig κ chain gene (hereinafter referred to as "TC(W23)/ΔH/Δκ") as well as the genetic background of the endogenous Ig heavy chain and κ chain knock-out mouse described in the report by Tomizuka et al. (Proc. Natl. Acad. Sci. USA., vol. 97, 722-727, 2000) and TC (ΔHAC)/ΔH/Δκ lineage produced in Example 15 were analyzed for the genotype in the same manner as in Example 15.

As a result, individuals were obtained which simultaneously carried ΔHAC and hCF(W23) and were homozygotes for the endogenous Ig heavy chain knock-out and homozygotes for the endogenous Ig κ chain knock-out (hereinafter referred to as "TC(ΔHAC)/TC(W23)/ΔH/Δκ").

Further, serum of TC(ΔHAC)/TC(W23)/ΔH/Δκ individuals can be analyzed by ELISA as described in the report by Tomizuka et al. (Proc. Natl. Acad. Sci. USA., vol. 97, 722-727, 2000) and the report by Kuroiwa et al. (Nature Biotechnol., 18; 1086-, 2000). Thus, expression of the human Ig μ chain, γ chain, λ chain, and κ chain proteins are respectively detected.

EXAMPLE 17

Construction of Mouse Lineage Carrying Yeast Artificial Chromosome Containing ΔHAC and Human Ig κ Chain Gene and Having Alleles of Endogenous Both Ig Heavy Chain and κ Chain Genes Destructed Individual mice obtained by crossing between a mouse lineage carrying a transgene containing human Ig κ chain gene (KCo5: containing about 40% of the variable region in the human κ light chain gene) as well as the genetic background of the endogenous Ig heavy chain and κ chain knock-out mouse described in the report by Fishwild et al. (Nature Biotechnol., 14: 845-851, 1996) [obtained from Medarex, U.S.A., hereinafter referred to as "KCo5/ΔH/Δκ"] and TC(ΔHAC)/ΔH/Δκ lineage produced in Example 15 were analyzed for the genotype by PCR and ELISA in the same manner as in Example 15.

As a result, individuals were obtained which simultaneously carried ΔHAC and KCo5 and were homozygotes for the endogenous. Ig heavy chain knock-out and homozygotes for the endogenous Ig κ chain knock-out (hereinafter referred to as "TC(ΔHAC)/KCo5/ΔH/Δκ").

Microorganisms retaining a yeast artificial chromosome or a plasmid constituting the transgene KCo5 are deposited at ATCC (U.S.A.). The accession numbers are as follows. Yeast retaining yeast artificial chromosome y17: ATCC No. PTA-3842, *Escherichia coli* retaining plasmid pKV4: ATCC No. PTA-3843, *Escherichia coli* retaining plasmid pKCIB: ATCC No. PTA-3844.

Serum of TC(ΔHAC)/KCo5/ΔH/Δκ individuals was analyzed by ELISA in the same manner as in Example 16, and as a result, human Ig μ chain, γ chain, λ chain, and κ chain proteins were detected. The average values for the γ chain in the assayed 3 individuals were higher than those for the μ chain.

EXAMPLE 18

Production of Anti G-CSF Antibody in the Mouse Lineage TC(ΔHAC)/ΔH/Δκ

Two individual TC(ΔHAC)/ΔH/Δκ mice produced in Example 15 were immunized with human G-CSF. TiterMaxGold (CytRx) was used as an adjuvant. First, 37.5 μg in total of human G-CSF was immunized subcutaneously in three separate sites. Then, the second and third times, 10 μg in total was immunized subcutaneously in three separate sites as with the initial immunization, 14 days and 38 days after the initial immunization respectively. The final immunization 48 days after the initial immunization was carried out by intravenous injection of 10 μg of G-SF without any adjuvant. Blood sampling was carried out 3 days after the final immunization and the values for the anti G-CSF human Ig G antibody and for the human Ig λ antibody in serum were measured by ELISA as described in the report by Kuroiwa et al. (Nature Biotechnol., 18: 1086-, 2000). As a result, an increase in the values for the anti human G-CSF human Ig G antibody and for the human Ig λ antibody was observed in both of the individuals.

Further, by screening by ELISA a hybridoma obtained by fusion between a spleen cell of the immunized individual mouse and a mouse myeloma cell (Ando, Chiba, "Tan kurohn Koutai Jikken Sousa Nyuumon (Monoclonal Antibody Experimentation and Manipulation Introduction)," Kodansha Scientific, 1991), a hybridoma producing a complete human monoclonal antibody comprising human Ig heavy chain and light chain λ can be obtained.

EXAMPLE 19

Production of Anti G-CSF Antibody in Mouse Lineage TC(ΔHAC)/TC(W23)/ΔH/Δκ

The individual mouse TC(ΔHAC)/TC(W23)/ΔH/Δκ produced in Example 16 was immunized with human G-CSF in the same manner as in Example 18. The values for the anti G-CSF human Ig G antibody, human Ig λ antibody, and human Ig κ antibody in serum of this mouse are measure by ELISA to confirm an increase in the values for the anti human G-CSF human Ig G antibody, human Ig λ antibody, and human Ig κ antibody.

In the same manner as in Example 18, a hybridoma producing a complete human monoclonal antibody comprising the human Ig heavy chain and λ light chain or κ light chain can be further obtained by fusion between a spleen cell of the immunized individual mouse and a mouse myeloma cell.

EXAMPLE 20

Production of Anti G-CSF Antibody in Mouse Lineage TC(ΔHAC)/KCo5/ΔH/Δκ

The individual mouse TC(ΔHAC)/TC(W23)/ΔH/Δκ produced in Example 17 was immunized with human G-CSF in the same manner as in Example 18 to measure the values for the anti G-CSF human Ig G antibody, human Ig λ antibody, and human Ig κ antibody in serum by ELISA. As a result an increase in the values for the anti human G-CSF human Ig G antibody, human Ig λ antibody, and human Ig κ antibody was confirmed.

In the same manner as in Example 18, a hybridoma producing a complete human monoclonal antibody comprising the human Ig heavy chain and the λ light chain or κ light chain was further obtained by fusion between a spleen cell of the immunized individual mouse and a mouse myeloma cell.

All publications, patents and patent applications cited herein are incorporated herein by reference in their entirety.

INDUSTRIAL APPLICABILITY

The present invention provides a human artificial chromosome which retains a total region of the human antibody heavy chain and λ light chain genes and is genetically transmissible to the next generation with high efficiency. The present invention also provides a non-human animal which genetically transmits the human artificial chromosome to the next generation with high efficiency and an offspring thereof. Further, the present invention enables the production of a human antibody.

Free Text of Sequence Listing
SEQ ID NO: 1; description of artificial sequence: primer
SEQ ID NO: 2; description of artificial sequence: primer
SEQ ID NO: 3; description of artificial sequence: primer
SEQ ID NO: 4; description of artificial sequence: primer
SEQ ID NO: 5; description of artificial sequence: primer
SEQ ID NO: 6; description of artificial sequence: primer
SEQ ID NO: 7; description of artificial sequence: primer
SEQ ID NO: 8; description of artificial sequence: primer
SEQ ID NO: 9; description of artificial sequence: primer
SEQ ID NO: 10; description of artificial sequence: primer
SEQ ID NO: 11; description of artificial sequence: primer
SEQ ID NO: 12; description of artificial sequence: primer
SEQ ID NO: 13; description of artificial sequence: primer
SEQ ID NO: 14; description of artificial sequence: primer
SEQ ID NO: 15; description of artificial sequence: primer
SEQ ID NO: 16; description of artificial sequence: primer

The invention claimed is:

1. A chimeric human antibody-producing mouse, wherein the antibody-producing mouse carries (1) human artificial chromosome ΔHAC or ΔΔHAC in which a 2.5 Mb region (ΔHAC) or a 1.5 Mb region (ΔΔHAC) from human chromosome 22 containing an unrearranged human antibody λ light chain locus is linked to a human chromosome 14 fragment containing an unrearranged human antibody heavy chain locus and (2) an unrearranged human antibody κ light chain transgene retained on KCo5 that is inserted into a mouse chromosome of the human antibody-producing mouse, at least both alleles of endogenous antibody heavy chain and κ light chain are disrupted or inactivated, and a human antibody heavy chain comprising a human antibody Ig γ isotype, a human antibody κ light chain, and a human antibody λ light chain are expressed in serum;

wherein at least 85% of the cells of the human antibody-producing mouse retain the human artificial chromosome ΔHAC or ΔΔHAC.

2. The human antibody-producing mouse according to claim 1, which carries at least 40% of the variable region of the human antibody κ light chain.

3. The human antibody-producing mouse according to claim 1, which carries all the variable regions of the human antibody heavy chain, the human antibody κ light chain, and the human antibody λ light chain.

4. The human antibody-producing mouse according to claim 1, wherein the human antibody κ light chain locus inserted into the mouse chromosome is derived from human chromosome 2.

5. The human antibody-producing mouse according to claim 1, wherein the human artificial chromosome is ΔΔHAC.

6. The human antibody-producing mouse according to claim 1, wherein the human artificial chromosome is ΔHAC.

7. The human antibody-producing mouse according to claim 1, wherein the human artificial chromosome is ΔΔHAC and 100% of the cells of the human antibody-producing mouse retain the human artificial chromosome.

8. A method for producing an antibody, which comprises: immunizing the mouse according to claim 1, and obtaining a polyclonal antibody from the mouse.

9. The method according to claim 8, wherein the polyclonal antibody is obtained from the blood of the mouse.

10. A method for producing an antibody, which comprises:
immunizing the mouse according to claim 1 with a desired antigen;
producing a hybridoma by fusing a mouse myeloma cell with a B cell derived from the mouse,
identifying the hybridoma that expresses a monoclonal antibody comprising human immunoglobulin heavy chains and light chains against the antigen, and producing the monoclonal antibody.

* * * * *

UNITED STATES PATENT AND TRADEMARK OFFICE
CERTIFICATE OF CORRECTION

PATENT NO. : 7,402,729 B2 Page 1 of 1
APPLICATION NO. : 11/151227
DATED : July 22, 2008
INVENTOR(S) : Yoshimi Kuroiwa et al.

It is certified that error appears in the above-identified patent and that said Letters Patent is hereby corrected as shown below:

ON THE TITLE PAGE:

Please change the Assignees Col. 1, line 13 to read:

-- Assignee: Medarex, Inc. (Princeton, NJ); Kirin Pharma Kabushiki Kaisha (Tokyo, JP) --

Signed and Sealed this

Seventh Day of July, 2009

JOHN DOLL
*Acting Director of the United States Patent and Trademark Office*